US009915632B2

(12) United States Patent
Owens et al.

(10) Patent No.: US 9,915,632 B2
(45) Date of Patent: Mar. 13, 2018

(54) LONG-RANGE MAGNETOSTRICTIVE ULTRASONIC GUIDED WAVE SCANNER SYSTEM AND METHOD

(71) Applicant: FBS, Inc., Bellefonte, PA (US)

(72) Inventors: Steven E. Owens, Bellefonte, PA (US); Cody J. Borigo, Port Matilda, PA (US); Li Zhang, State College, PA (US); Joseph L. Rose, State College, PA (US); Russell G. Love, Port Matilda, PA (US)

(73) Assignee: FBS, INC., Bellefonte, PA (US)

( * ) Notice: Subject to any disclaimer, the term of this patent is extended or adjusted under 35 U.S.C. 154(b) by 40 days.

(21) Appl. No.: 15/091,896

(22) Filed: Apr. 6, 2016

(65) Prior Publication Data

US 2016/0290965 A1 Oct. 6, 2016

Related U.S. Application Data

(60) Provisional application No. 62/143,458, filed on Apr. 6, 2015.

(51) Int. Cl.
*G01N 27/82* (2006.01)
(52) U.S. Cl.
CPC .................... *G01N 27/82* (2013.01)
(58) Field of Classification Search
None
See application file for complete search history.

(56) References Cited

U.S. PATENT DOCUMENTS

| 4,137,470 A | | 1/1979 | Désormiére et al. |
| 4,195,530 A | * | 4/1980 | Ross ............... G01N 29/26 73/638 |
| 4,356,731 A | | 11/1982 | Mahony |
| 5,260,615 A | | 11/1993 | Sahashi et al. |
| 5,581,037 A | * | 12/1996 | Kwun ............... G01N 29/14 324/220 |

(Continued)

OTHER PUBLICATIONS

J.L., Ultrasonic Guided Waves in Solid Media, Cambridge University Press, (2014): 1-15, 269-275.

(Continued)

*Primary Examiner* — Patrick Assouad
*Assistant Examiner* — Demetrius Pretlow
(74) *Attorney, Agent, or Firm* — Duane Morris LLP

(57) ABSTRACT

A system for non-destructive inspection of a structure includes a magnetostrictive pulser coil and a ferromagnetic strip. The ferromagnetic strip is coupled to the structure adjacent to the pulser coil. A scanner receiver probe is located adjacent to the ferromagnetic strip. The probe includes a probe body, a position encoder, and a magnetostrictive partial loading receiver coil. A magnet applies a biasing magnetic field to the ferromagnetic strip. A pulser system generates a time-varying current in the pulser coil to induce a time-varying magnetization in the ferromagnetic strip to generate guided wave energy in the structure. The probe detects reflected guided wave energy as the probe is moved around the circumference of the structure. A processor controls the pulser system, records guided wave reflections, and process the guided wave and probe position data to generate a one-dimensional image or a two-dimensional image of anomalies in said structure.

19 Claims, 24 Drawing Sheets

(56) References Cited

U.S. PATENT DOCUMENTS

| | | | |
|---|---|---|---|
| 5,619,423 A * | 4/1997 | Scrantz | G01N 29/2412 324/220 |
| 5,679,898 A * | 10/1997 | Schlawne | G01N 29/041 73/622 |
| 5,841,277 A | 11/1998 | Hedengren et al. | |
| 5,907,100 A * | 5/1999 | Cook | G01N 29/2412 73/602 |
| 6,125,703 A * | 10/2000 | MacLauchlan | G01N 29/0609 73/592 |
| 6,148,672 A | 11/2000 | Cawley et al. | |
| 6,299,703 B1 | 10/2001 | Chen et al. | |
| 6,429,650 B1 | 8/2002 | Kwun et al. | |
| 6,624,628 B1 | 9/2003 | Kwun et al. | |
| 6,813,950 B2 | 11/2004 | Glascock et al. | |
| 6,917,196 B2 | 7/2005 | Kwun et al. | |
| 7,375,514 B2 | 5/2008 | Rempt et al. | |
| 7,573,261 B1 | 8/2009 | Vinogradov et al. | |
| 7,614,313 B2 | 11/2009 | Kim et al. | |
| 7,821,258 B2 | 10/2010 | Vinogradov et al. | |
| 7,852,073 B2 * | 12/2010 | Kwun | G01N 27/82 324/238 |
| 7,913,562 B2 | 3/2011 | Kwun et al. | |
| 7,997,139 B2 | 8/2011 | Owens et al. | |
| 8,354,842 B2 | 1/2013 | Kim et al. | |
| 8,653,810 B2 | 2/2014 | Cobb et al. | |
| 8,907,665 B2 | 12/2014 | Rose et al. | |
| 9,074,995 B2 | 7/2015 | Cho et al. | |
| 2004/0139792 A1 * | 7/2004 | Cobb | G01N 29/032 73/61.75 |
| 2010/0199770 A1 * | 8/2010 | Kleinert | G01N 29/0645 73/628 |
| 2012/0119732 A1 * | 5/2012 | Rose | G01N 29/2412 324/240 |

OTHER PUBLICATIONS

Trémolet de Lacheisserie, E., Magnetostriction: Theory and Applications of Magnetoelasticity, CRC press, (1993): 339-352, 359-361.

Sun, Z., Zhang, L., & Rose, J. L., "Flexural torsional guided wave mechanics and focusing in pipe," Journal of Pressure Vessel Technology, 127.4 (2005): 471-478.

Davies, J. and Cawley, P., "The Application of Synthetic Focusing for Imaging Crack-Like Defects in Pipelines Using Guided Waves," IEEE Transactions on Ultrasonics, Ferroelectrics, and Frequency Control, 56.4 (2009): 759-771.

Sicard, R., Goyette, J., and Zellouf, D., "A SAFT Algorithm for Lamb Wave Imaging of Isotropic Plate-Like Structures," Ultrasonics, 39 (2002):487-494.

Sicard, R., Chahbaz, A., and Goyette, J., "Guided Lamb Waves and L-SAFT Processing Technique for Enhanced Detection and Imaging of Corrosion Defects in Plates with Small Depth-to-Wavelength Ratio," IEEE Transactions on Ultrasonics, Ferroelectrics, and Frequency Control, 51.10 (2004): 1287-1297.

Kuokkala, V.T. and Schwarz, R.B., "The use of magnetostrictive film transducers in the measurement of elastic moduli and ultrasonic attenuation of solids," Rev. Sci. Instrum., 63(5), pp. 3136-3142, 1992.

Joule, J.P., "On the effects of magnetism upon the dimensions of iron and steel bars," Phil. Mag., Series 3, 30(199), pp. 76-87, 1842.

U.S. Appl. No. 15/043,092, filed Feb. 12, 2016.

* cited by examiner

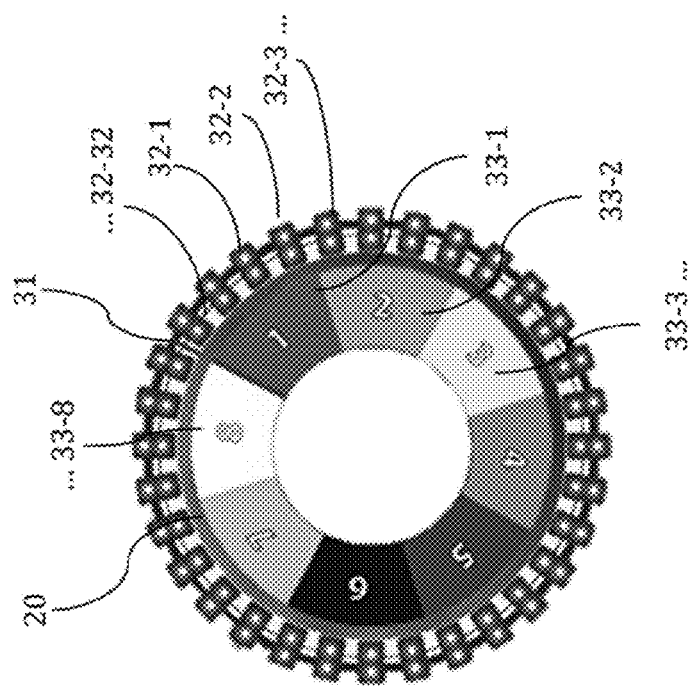
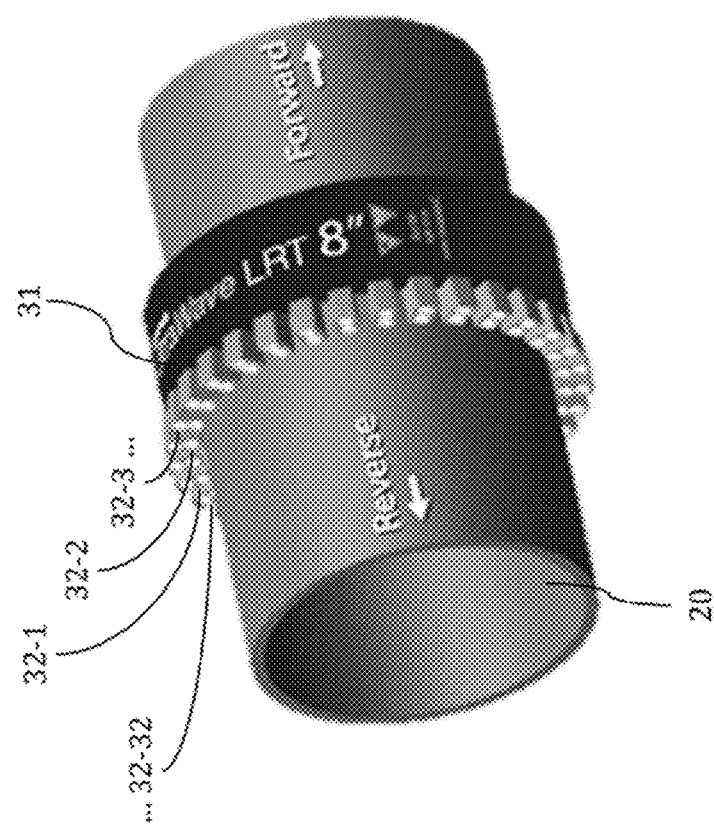
Fig. 3

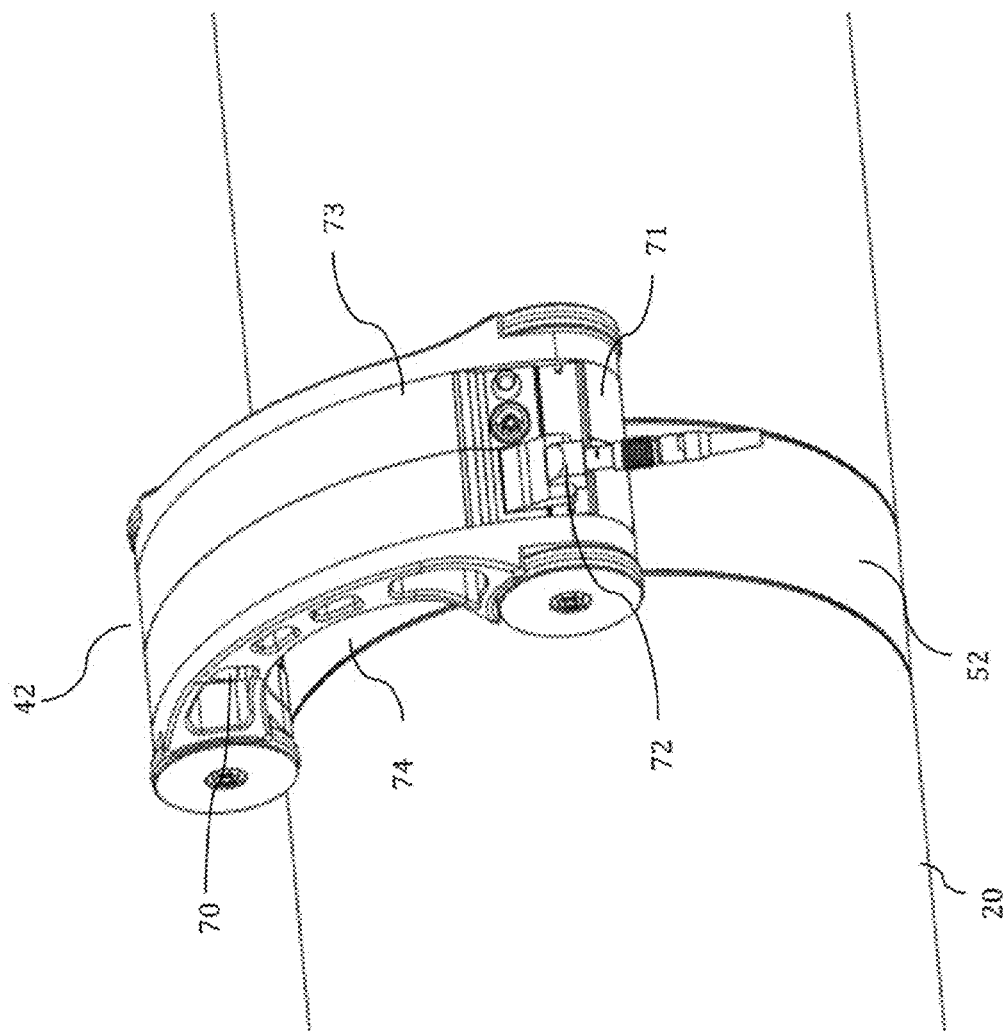

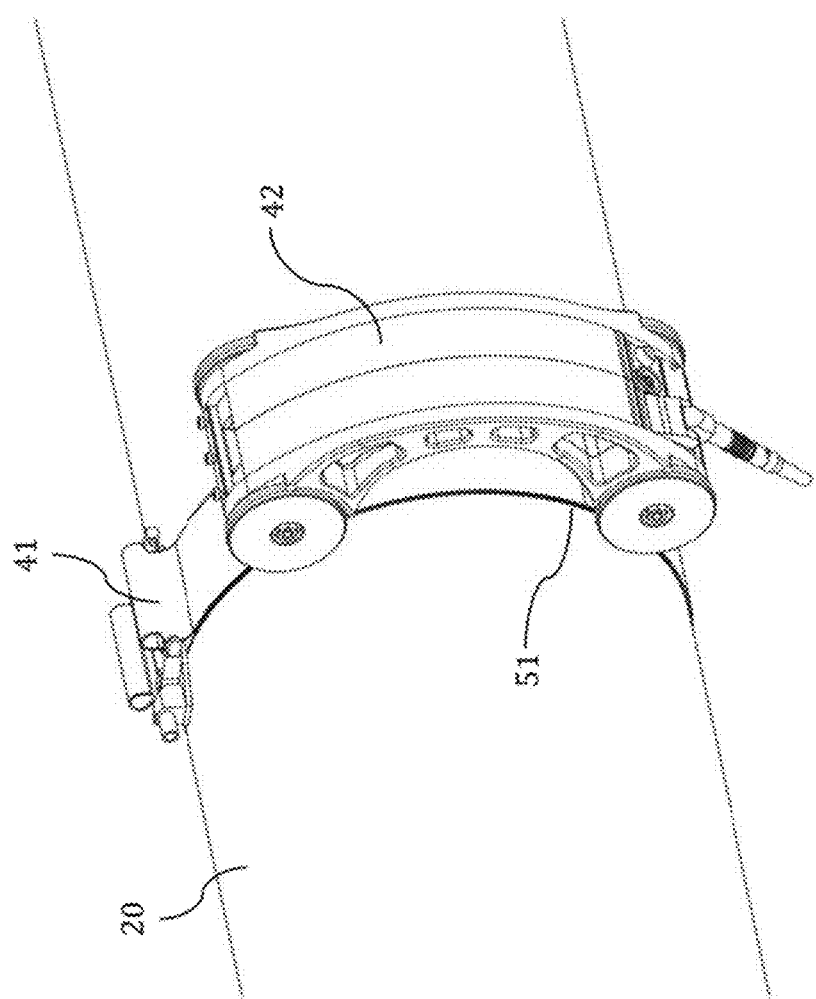

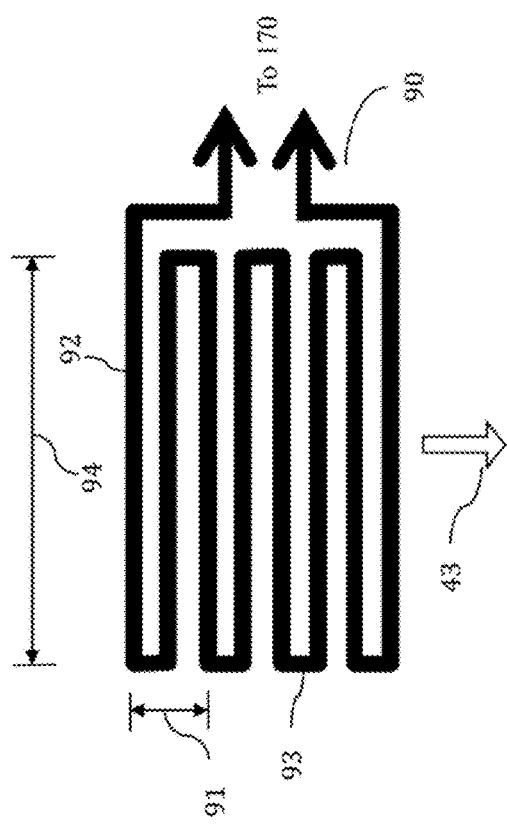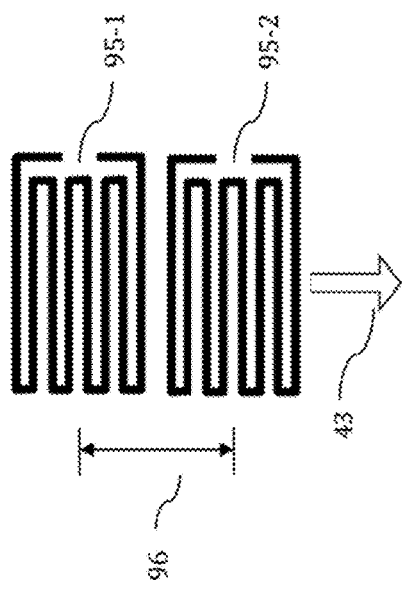

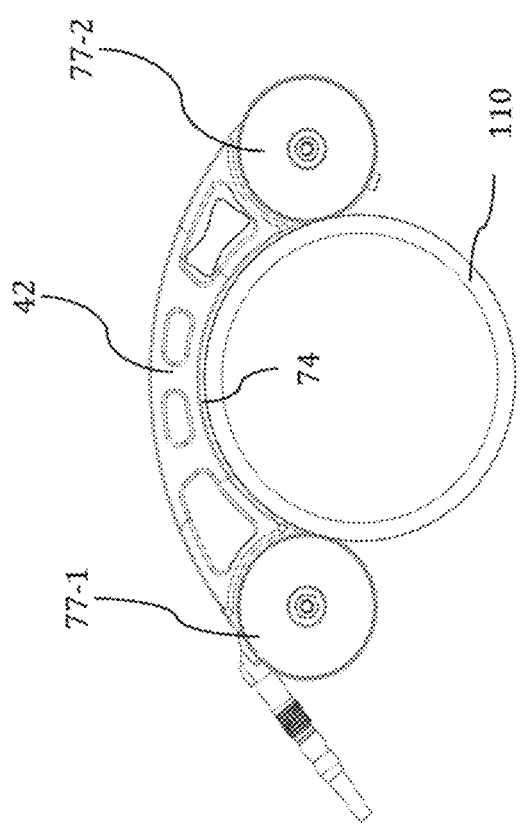

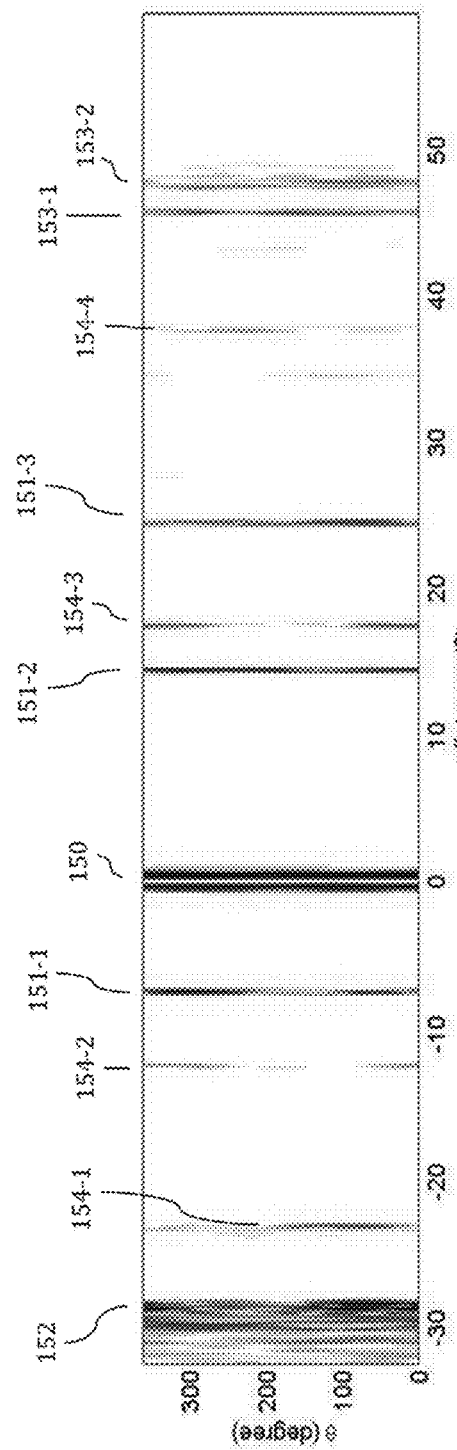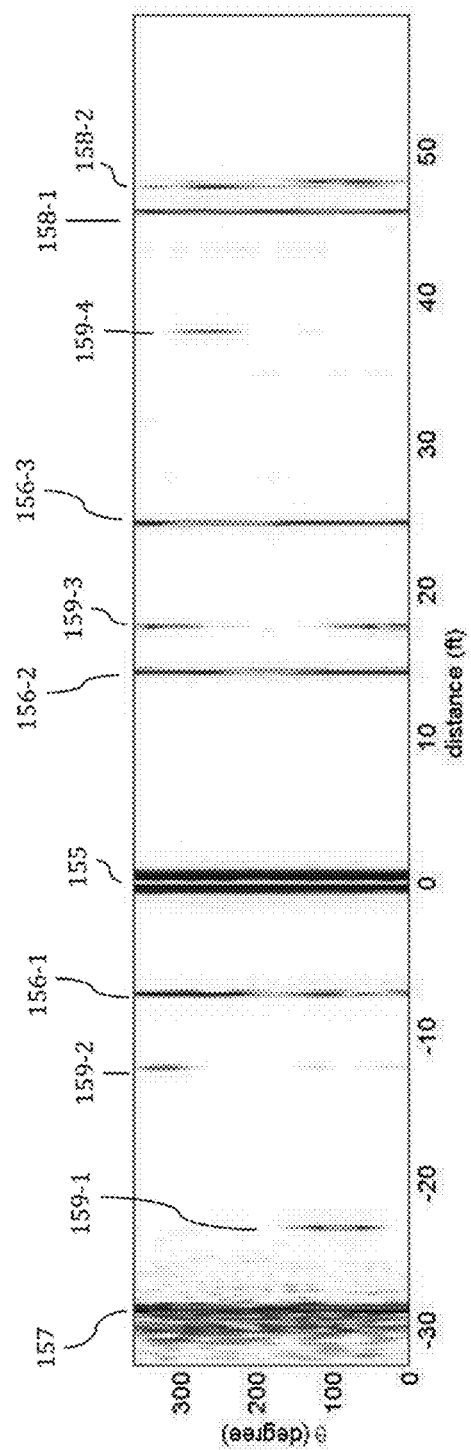

LONG-RANGE MAGNETOSTRICTIVE ULTRASONIC GUIDED WAVE SCANNER SYSTEM AND METHOD

CROSS-REFERENCE TO RELATED APPLICATIONS

This application claims priority to U.S. Provisional Patent Application No. 62/143,458, filed Apr. 6, 2015, and entitled "A LONG-RANGE MAGNETOSTRICTIVE ULTRASONIC GUIDED WAVE SCANNER SYSTEM AND METHOD," which is incorporated by reference herein in its entirety.

FIELD

This disclosure relates to the non-destructive inspection of sections of pipes, tubes, cylinders, and cylindrical vessels using ultrasonic guided waves.

BACKGROUND INFORMATION

Ultrasonic guided wave techniques are utilized in a wide range of non-destructive inspection applications including those for pipes, plates, and shells comprised of metals, composites, and other materials. Guided waves are elastic waves propagating in a bounded structure that is utilized as a waveguide to efficiently transmit one or more wave modes along the structure. One of the foremost benefits of guided waves over other non-destructive inspection techniques is the ability of said waves to propagate over long distances, in many cases, hundreds of feet, and to inspect inaccessible or hidden structures from a single probe position.

Long-range guided wave techniques are often utilized for the inspection of pipelines; however, focusing-capable systems are often complex and costly due to the need for segmentation of the transducer collar. Segmentation allows the sound to be sent and received in a partial loading configuration around the circumference of the pipe. Partial receiving and, in some cases, partial loading are required to perform both active and synthetic focusing of guided wave energy in the pipe to identify the axial and circumferential location and extent of reflectors. Segmentation of the collar also makes it difficult for the transducer collars to provide axisymmetric loading, as the segmentation often leaves inactive zones between the segments. Conventional focusing-capable long-range guided wave pipeline inspection systems typically utilize complex multi-channel phased array pulser/receiver electronics capable of sending and receiving guided waves over many channels, typically 16-24, to support transducer collars arranged into 8 segments. In the case of synthetic focusing, it would be most ideal to send an axisymmetric wave and then be able to receive with partial loading. It would also be advantageous in some cases to be able to increase the number of receiving locations around the circumference of the pipe without having more channels in the pulser/receiver electronics and more segments in the transducer collar. It would further be advantageous to be able to have a system in which the aperture within the segments can be larger or smaller than the length of the circumference divided by the number of circumferential channels, which manifests as partial receiver section overlap.

SUMMARY

In some embodiments, a non-destructive inspection system for pipes, tubes, cylinders, and cylindrical vessels includes a magnetostrictive pulser collar, at least one ferromagnetic strip, a partial loading magnetostrictive scanner receiver probe, at least one magnet, at least one wheel configured to move said receiver probe around said structure, an electronic pulser system, a means for detecting reflected guided wave energy via said receiver probe, and a processor. The scanner receiver probe includes a probe body, a magnetostrictive receiver coil, and a position encoder. At least one ferromagnetic strip is configured to be coupled to said structure adjacent to the pulser collar and at least one ferromagnetic strip is configured to be coupled to said structure adjacent to the scanner receiver probe. The at least one magnet, which may be a permanent magnet or an electromagnet, is configured to apply a biasing magnetization to the at least one strip. The electronic pulser system is configured to generate an axisymmetric guided wave pulse from the pulser collar. The processor is configured to control said electronic pulser system, record guided wave reflections via the partial loading scanner receiver probe, and process the guided wave and scanner receiver position data to generate at least one of a one-dimensional image and a two-dimensional image of anomalies in said structure.

In some embodiments, a method for the non-destructive inspection of pipes, tubes, cylinders, and cylindrical vessels includes applying a biasing magnetic field to at least one ferromagnetic strip, generating a time-varying current in a magnetostrictive pulser collar to generate axisymmetric guided waves in said structure, moving a magnetostrictive partial loading receiver scanner around said structure adjacent to at least one ferromagnetic strip, detecting guided wave reflections using said receiver scanner, and recording and processing guided wave and position data to generate at least one of a one-dimensional image and a two-dimensional image of anomalies in said structure.

BRIEF DESCRIPTION OF THE DRAWINGS

FIG. 3 is an illustration of a conventional long-range guided wave pipe inspection collar.

FIG. 7a is an illustration of one embodiment of the scanning receiver applied to a pipe.

FIG. 8 is an illustration of one embodiment of the system in which the pulser collar and scanning receiver are collocated on a pipe.

FIG. 9a is an illustration of one embodiment of a pulser/receiver coil.

FIG. 9b is an illustration of one embodiment of a pair of pulser/receiver coils implemented for directional wave control.

FIG. 11a is an illustration of one embodiment of the scanning receiver applied to a 4" NPS pipe.

FIG. 15a is an example of a two-dimensional synthetic focusing image of an 80'-long 8" pipe loop generated with a conventional long-range guided wave pipe inspection system and method.

FIG. 15b is an example of a two-dimensional synthetic focusing image of an 80'-long 8" pipe loop generated with the disclosed system and method.

FIG. 17a is a conceptual diagram of a second embodiment of the system electronics.

DETAILED DESCRIPTION

Figure 1:
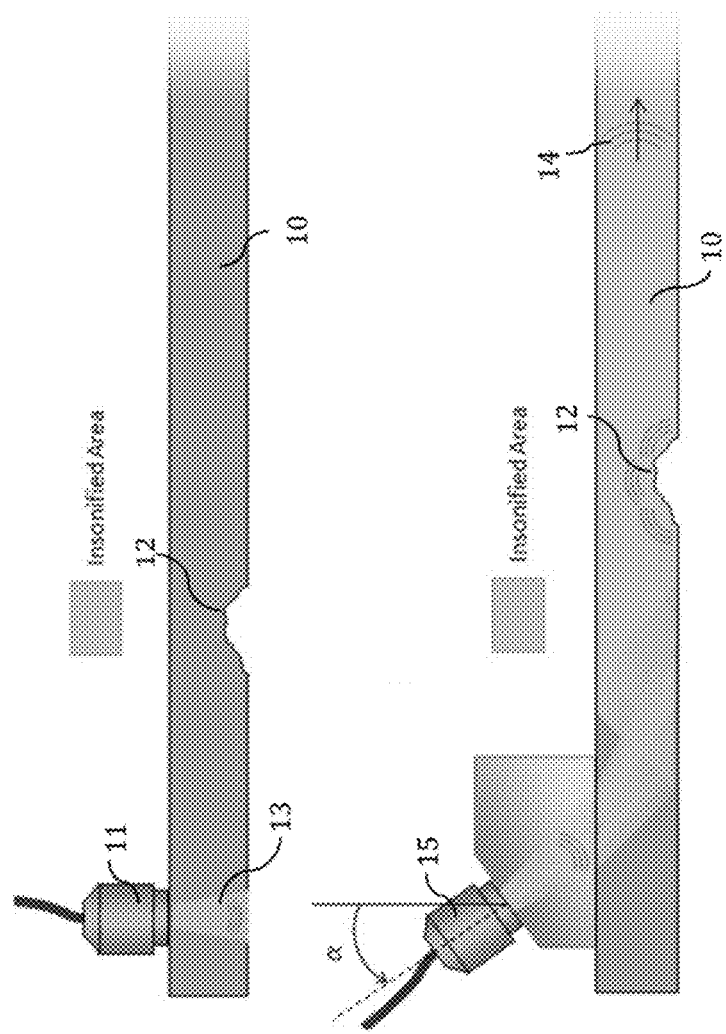
FIG. 1 is a conceptual illustration of the differences between ultrasonic bulk waves and ultrasonic guided waves.

This description of the exemplary embodiments is non-limiting and is intended to be read in connection with the accompanying drawings, which are to be considered part of the entire written description.

Guided waves are formed from the constructive interference of ultrasonic bulk waves that have interacted with the boundaries of the structure in which they propagate. A conceptual illustration is provided in FIG. 1. In this illustration, an ultrasonic transducer is used to generate either bulk waves or guided waves to detect the corrosion defect. Guided waves are unique in the sense that they are capable of propagating for long distances compared to traditional ultrasonic waves and can be used to inspect hidden/inaccessible structures like buried or cased piping and tubing. Unlike "spot-checking" with traditional ultrasonic techniques, guided waves provide a 100% volumetric inspection. Furthermore, guided waves provide an efficient and cost-effective means of inspection due to increased inspection speed and simplicity.

Various means of guided wave transduction exist including piezoelectric transducers, electromagnetic acoustic transducers (EMATs), impact devices, and magnetostrictive transducers. Magnetostrictive transducers have been utilized for the purposes of ultrasonic guided wave generation for many decades and have more recently been utilized for the purposes of long-range pipe inspection. Long-range guided wave pipe inspection systems can inspect pipelines over distances of up to several hundred feet in each direction from a fixed transducer collar location and have been implemented using various means.

For the purposes of the description, the term "pipe" refers to hollow cylinders including, but not limited to, structures such as pipes, tubes, cylinders, and cylindrical vessels.

For the purposes of the description, the term "torsional guided waves" refers to the class of torsional sonic/ultrasonic guided stress waves in hollow cylinders, which have predominantly in-plane displacement fields perpendicular to the wave propagation direction. This term encompasses axisymmetric T(0, n) and non-axisymmetric, i.e. flexural, T(m≠0, n) modes in the torsional mode families of guided waves in hollow cylinders.

For the purposes of the description, the term "longitudinal guided waves" refers to the class of longitudinal sonic/ultrasonic guided stress waves in hollow cylinders, which have predominantly out-of-plane displacement fields and in-plane displacement fields parallel to the wave propagation direction. This term encompasses axisymmetric L(0, n) and non-axisymmetric, i.e. flexural, L(m≠0, n) modes in the longitudinal mode families of guided waves in hollow cylinders.

For the purposes of the description, the term "axisymmetric guided wave" refers to guided wave energy that is generally uniform around the circumference of the pipe, e.g. the T(0,n) or L(0,n) modes. Although pure axisymmetric mode excitation may be impossible in practice due to imperfections in loading patterns and amplitudes around the circumference of said pipe, quasi-axisymmetric waves can be effectively considered to be axisymmetric when interpreting and processing the data, especially after these waves have propagated a short distance away from the excitation source. Axisymmetric or quasi-axisymmetric excitation on a pipe predominantly excites the axisymmetric modes in said pipe.

For the purposes of the description, the term "partial loading" refers to at least one of generating and receiving guided waves in a pipe with a transducer that covers an incomplete portion of the circumference of the pipe. Partial loading excitation on a pipe excites a combination of guided wave modes in said pipe with the total energy divided among the various axisymmetric and flexural modes. Partial loading receiving on a pipe is analogously capable of detecting any of said axisymmetric flexural guided wave modes propagating in said pipe.

In some embodiments, a long-range magnetostrictive ultrasonic guided wave system that generates at least one of A-scans and synthetic focusing scan images for the purpose of non-destructive inspection of pipes by sending and receiving guided waves in said pipes is disclosed. In some embodiments a method for acquiring the requisite guided wave data using said system and generating at least one of said A-scans and synthetic focusing scans of said pipes is disclosed.

In some embodiments, a magnetostrictive guided wave pipeline inspection system and method that utilizes a static axisymmetric pulser collar and a moveable receiving sensor to avoid the need for more complex and expensive segmented pulser/receiver collars and associated multi-channel pulser/receiver electronics is disclosed. The magnetostrictive guided wave pipeline inspection system is less complex and less costly than conventional multi-channel guided wave pipe inspection systems and produces A-scans and synthetic focusing scans for the purpose of non-destructive inspection that are of equal or greater quality than conventional systems. In addition to the cost-effectiveness and improved resolution, the magnetostrictive guided wave pipeline inspection system can also be manufactured in a dramatically smaller and lighter form factor than conventional long-range guided wave pipe inspection systems, which makes simpler for the user to transport the equipment.

In some embodiments, a magnetostrictive ultrasonic guided wave axisymmetric pulser collar is disclosed. The magnetostrictive ultrasonic guided wave axisymmetric pulser collar includes at least one independent pulsing coil, a circumferential magnetostrictive scanner receiver having at least one independent sensor coil and covering a portion of the circumference of the pipe, a position encoder mounted on the scanner receiver, at least one ferromagnetic strip, a means of applying a biasing magnetic field to the at least one said strip, a means of generating guided wave pulses in a pipe via said pulser collar, a means of measuring guided wave signals detected by said receiver, a means of correlating received data with the circumferential location of said receiver on said pipe, a means of saving said data on a machine-readable storage medium, a means of processing said data to generate at least one of A-scans and synthetic focusing scans for the purpose of non-destructive inspection of pipes, and a means of controlling the system hardware and software. The disclosed magnetostrictive guided wave pipeline inspection system is less complex and less costly than conventional multi-channel guided wave pipe inspection systems and produces A-scans and synthetic focusing scans for the purpose of non-destructive inspection that are of equal or greater quality than conventional systems.

The disclosed magnetostrictive guided wave pipeline inspection system includes magnetostrictive ultrasonic guided wave axisymmetric pulser collar having at least one independent pulsing coil, a circumferential magnetostrictive scanner receiver having at least one independent sensor coil and covering a portion of the circumference of the pipe, a position encoder mounted on the scanner receiver, at least one ferromagnetic strip, a means of applying a biasing magnetic field to the at least one said strip, a means of generating guided wave pulses in a pipe via said pulser collar, a means of measuring guided wave signals detected by said receiver, a means of correlating received data with the circumferential location of said receiver on said pipe, a means of saving said data on a machine-readable storage medium, a means of processing said data to generate at least one of A-scans and synthetic focusing scans for the purpose of non-destructive inspection of pipes, and a means of controlling the system hardware and software. The disclosed magnetostrictive guided wave pipeline inspection system is less complex and less costly than conventional multi-channel guided wave pipe inspection systems and produces A-scans and synthetic focusing scans for the purpose of non-destructive inspection that are of equal or greater quality than conventional systems.

The magnetostrictive guided wave pipeline inspection system is operated by placing an axisymmetric or quasi-axisymmetric magnetostrictive pulser collar adjacent to at least one associated ferromagnetic strip that is coupled to a pipe, placing a magnetostrictive partial loading scanner receiver adjacent to at least one associated ferromagnetic strip that is also coupled to said pipe, applying biasing magnetization to said ferromagnetic strips, and generating a guided wave in the pipe via the pulser collar while simultaneously scanning the partial loading receiver around the pipe to collect reflected guided wave data at multiple circumferential locations along the at least one ferromagnetic strip, by which a series of axisymmetric guided wave signals are transmitted in at least one direction along the pipe and a series of waveforms, which are representative of reflected guided wave energy from features in the pipe, are collected with the scanning partial loading receiver. The collected waveforms are processed in conjunction with position encoder data from the scanner to produce at least one of axial A-scans and synthetic focusing scans, which provide information on the axial and circumferential location and extent of features in the pipe and are generated using a modal decomposition and back-propagation algorithm.

The magnetostrictive guided wave pipeline inspection system is operated by placing an axisymmetric or quasi-axisymmetric magnetostrictive pulser collar adjacent to the at least one ferromagnetic strip that is coupled to a pipe, placing a magnetostrictive partial loading scanner receiver adjacent to the at least one ferromagnetic strip that is also coupled to said pipe, applying biasing magnetization to at least one said ferromagnetic strip, and generating a guided wave in the pipe via the pulser collar while simultaneously scanning the partial loading receiver around the pipe circumference along at least one said ferromagnetic strip to collect reflected guided wave data at multiple circumferential positions. By this means, a series of axisymmetric guided wave signals are transmitted in at least one direction along the pipe and a series of waveforms, which are representative of reflected guided wave energy from features in the pipe, are collected with the scanning partial loading receiver and correlated with position encoder data from said scanning receiver. The collected waveforms are processed in conjunction with position encoder data from the scanner to produce at least one of axial A-scans, which are generated using the guided wave data and the known wave velocity in the pipe, and synthetic focusing scans, which provide information on the axial and circumferential location and extent of features in the pipe and are generated using a modal decomposition and back-propagation algorithm. An example modal decomposition and back-propagation algorithm is discussed below:

The reflected wave field from an axisymmetric wave input u can be described as:

$$u(\theta, z, t) = \sum_{\omega=-\infty}^{\infty} \sum_{m=-\infty}^{+\infty} A(m, \omega) e^{i(m\theta + k_m z + \omega t)},$$

where m is circumferential order, $\omega$ is frequency, $k_m$ is the wave number of mode T(m, 1), $A(m, \omega)$ is the amplitude of mode T(m, 1) reflected by the defect at frequency $\omega$. Assuming that N is the total number of receivers in the circumferential direction located at z=0 and $\theta=\theta_i$, (i=0, 1, ..., N−1), the signal received by the $i^{th}$ receiver $u_R(\theta_i, t)$ can be written as:

$$u_R(\theta_i, t) = \sum_{\omega=-\infty}^{\infty} \sum_{m=-\infty}^{+\infty} A(m, \omega)e^{i(m\theta_i+\omega t)}.$$

Here the received signal $u_R(\theta_i, t)$ is a function of circumferential position of the receiver $\theta_i$ and time t. Performing a 2D fast Fourier transform (FFT) on both sides of Eq. (2) in the circumferential spatial and the time domains, one can obtain the amplitudes of the reflected modes through the 2D FFT decomposition process. The pipe image can then be reconstructed from the following back-propagation process:

$$u_s(\theta, z) = \sum_{\omega=\omega_1}^{\omega_l} \sum_{m=0}^{N} A(m, \omega)e^{i(k_n z + m\theta)},$$

where $\omega_1, \omega_2, \ldots, \omega_l$ are the discrete frequency contents within the effective frequency bandwidth, $\theta$ and z are pipe circumferential and axial locations respectively; us is the reconstructed pipe image from synthetic focusing. Although specific embodiments are discussed herein, it will be appreciated that other modal decomposition and back-propagation algorithms can be used.

The magnetostrictive guided wave pipeline inspection system generates guided waves via the magnetostrictive effect, i.e. the Joule effect, by which a time-varying strain is induced in the ferromagnetic material by means of generating a time-varying current in a pulser coil in the presence of a biasing magnetic field that is perpendicular to the direction of wave propagation to generate shear-horizontal type waves, e.g. torsional waves in pipes, or parallel to the direction of wave propagation to generate Lamb-type waves, e.g. longitudinal waves in pipes. The coil traces are oriented in a manner such that they induce a time-varying magnetic field in the ferromagnetic material that is parallel to the wave propagation direction and the axis of the pipe. By this process, guided waves are generated in the structure to which the ferromagnetic material is coupled.

In some embodiments, the magnetostrictive guided wave pipeline inspection system generates and detects guided wave modes in the T(n,1) family, the L(n,2) family, and/or any other suitable family or combination of families. The magnetostrictive guided wave pipeline inspection system may be switched between generating and receiving torsional and longitudinal modes by reorienting the biasing magnets in the system. In some inspection scenarios, one type of guided wave mode may feature advantages over the other, and thus the ability to rapidly select and adjust the system for either type of guided wave mode excitation is advantageous.

The guided waves propagate through the structure away from the pulser coil, and reflected wave energy from any structural anomalies is subsequently detected by the scanner receiver via the inverse magnetostrictive effect, i.e. the Villari effect, in which the passing stress waves induce a time-varying magnetic field in the ferromagnetic strip, which induces a time-varying current in the receiver coil.

The coupling of said ferromagnetic strips to said pipe may be achieved by means of at least one of shear couplant, bonding, brazing, adhesive taping, and mechanical pressure coupling.

The biasing magnetization of the at least one ferromagnetic strip adjacent to the pulser coil may be achieved by swiping the material with a permanent magnet prior to the scan or by utilizing at least one permanent magnet or electromagnet. The biasing magnetization of the at least one ferromagnetic strip adjacent to the receiver scanner may be achieved by swiping the material with a permanent magnet prior to the scan or by utilizing at least one permanent magnet built into the receiver probe body, which magnetizes the material as the probe is scanned along the structure.

The at least one pulser and receiver coils may be a flat-flexible cable or a flexible printed circuit board. The at least one pulser and receiver coils may be interchangeable to generate and receive guided waves across a wide range of frequencies between 10 kHz and 2 MHz.

The axisymmetric pulser and the partial loading receiver each utilize at least one ferromagnetic strip. In some embodiments, the pulser and receiver may share said ferromagnetic strips or they may utilize separate strips. In embodiments in which the pulser and receiver utilize separate ferromagnetic strips, said strips are coupled to the pipe at a fixed distance apart. In some embodiments, said separation distance is selected such that it is possible to directly receive the axisymmetric wave as it is generated and emitted along the pipe past the receiver coil; the direct wave signal may be used to calibrate the system by adjusting the signal for variations in coupling and magnetization around the circumference in the pipe or to measure the effectiveness of directional wave control.

Various embodiments of the system pulser/receiver electronics can be used to accomplish the means of sending axisymmetric guided waves and receiving guided wave reflections using partial loading around the circumference of the pipe. In some embodiments, the system pulser/receiver electronics comprise at least one ultrasonic tone-burst or square wave pulse generator, at least one analog-to-digital converter, at least one pre-amplifier, and at least one of phased array and multiplexing circuitry to facilitate generating guided waves from the at least one independent pulser coils and to facilitate receiving guided wave signals from the at least one independent receiver coils. U.S. patent application Ser. No. 15/043,092, filed Feb. 12, 2016, and entitled "MEDIUM-RANGE MAGNETOSTRICTIVE ULTRASONIC GUIDED WAVE SCANNER SYSTEMS AND METHODS" is incorporated by reference herein in its entirety.

By sending and receiving guided wave signals via at least two independent pulser coils separated by a known distance parallel to the axis of the pipe and two independent receiver coils separated by a known distance parallel to the axis of the pipe, directional wave control can be implemented by means of at least one of real-time time delays between said parallel coils using phased array hardware and artificial time delays between said parallel coils applied in post processing.

In some embodiments, in addition to the pulser/receiver electronics, the system further comprises a controller and a graphic user interface. The controller includes a machine-readable storage medium and a processor in signal communication with said machine-readable storage medium. The processor is configured to cause a pulse to be generated by the at least one sending magnetostrictive coil, measure the reflected signals detected by the at least one receiver magnetostrictive coil, process data collected at multiple locations around the circumference of said pipe, and save the waveforms and associated receiver position data in the machine-readable storage medium.

In some embodiments, the system software incorporates signal processing techniques to generate at least one of A-scans and two-dimensional synthetic focusing images of features in the pipe. The signal processing techniques utilized in the software include at least one of averaging, filtering, multi-frequency data acquisition, directional wave control, reverse wave suppression, modal decomposition, and synthetic focusing.

FIG. 1 compares a an ultrasonic "bulk wave" 13 and a ultrasonic "guided wave" 14 in a plate-like structure 10, which could be representative of, for example, a pipe wall. Both types of waves are capable of detecting corrosion 12, but the bulk wave transducer 11 must be located directly above the corrosion, as it only insonifies a localized region below it. The guided wave transducer 15, on the other hand, can be located remotely from corrosion 12 and still detect it since the guided wave 14 is capable of filling the entire cross-section of the structure 10 with energy that propagates some distance away from the transducer location. This capability of long-range propagation and remote detection is a great advantage for guided wave technologies.

Figure 2:
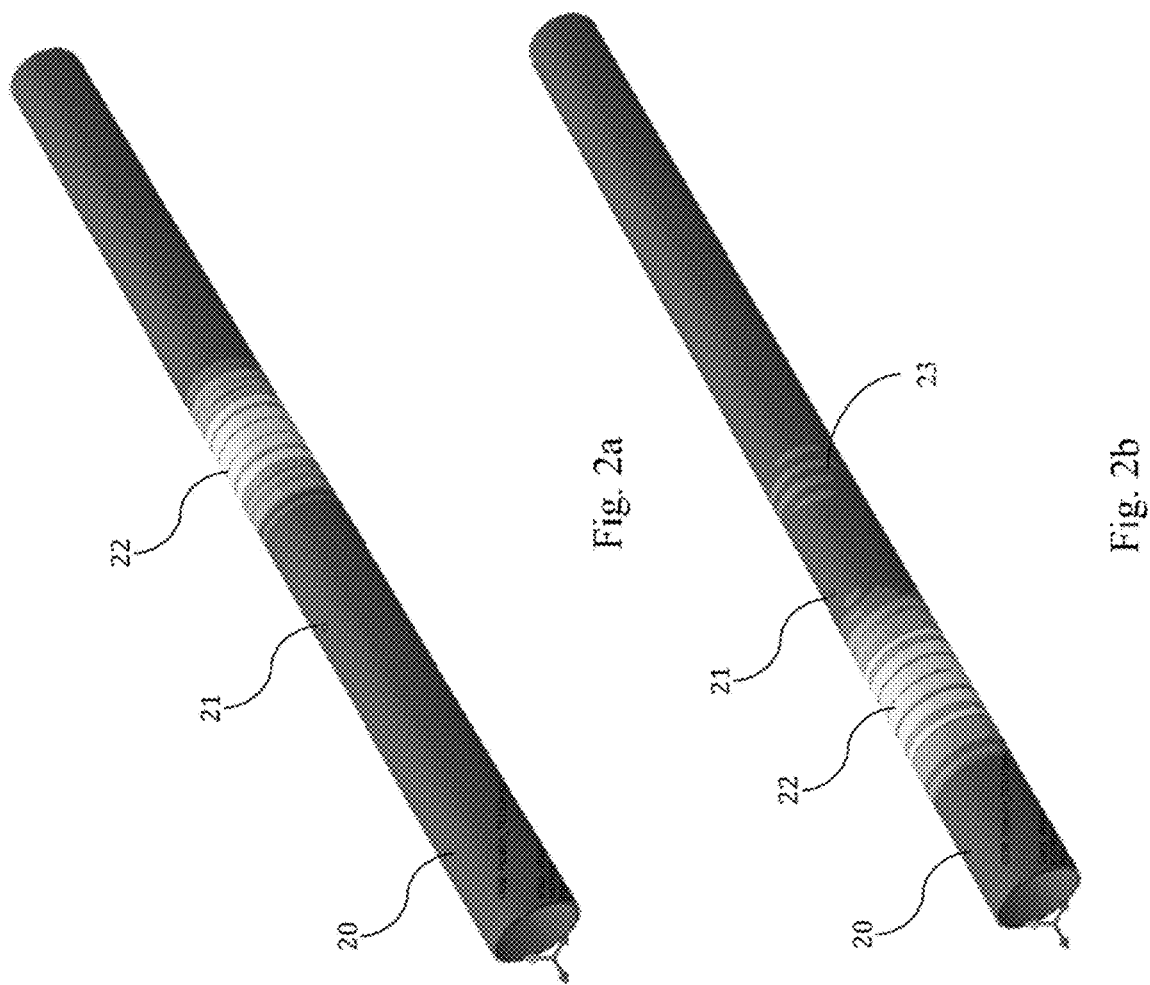
FIG. 2 is an illustration of axisymmetric and flexural guided waves in a pipe with a defect.

FIGS. 2a and 2b illustrate one embodiment of axisymmetric and flexural guided waves that are generated and detected by the magnetostrictive guided wave pipeline inspection system. FIG. 2a illustrates an axisymmetric guided wave 22 in a pipe 20. Axisymmetric wave 22 is generated by an axisymmetric pulser collar and propagates along the axis of the pipe with generally uniform energy distribution around the circumference. In FIGS. 2a and 2b, the axisymmetric wave is propagating from right to left toward corrosion defect 21 localized on the top of pipe 20. The magnetostrictive guided wave pipeline inspection system emits axisymmetric waves in order to have equal sensitivity to reflectors on all sides of the pipe. FIG. 2b shows that some fraction of the guided wave energy from axisymmetric wave 22 is reflected from defect 21 in the form of a generally non-axisymmetric (i.e. flexural) guided wave 23. The circumferential distribution of flexural guided wave 23 does not immediately reveal the circumferential location of defect 21; this is due to the fact that these flexural waves spiral around the pipe 20 as they propagate away from a non-axisymmetric reflector such as defect 21. In some embodiments, the magnetostrictive guided wave pipeline inspection system utilizes advanced post-processing algorithms to determine the location and size of defects in the pipe based on knowledge of the guided wave mechanics in the pipe and the circumferential distribution of the reflected wave field. Although the axisymmetric wave 22 may not be perfectly axisymmetric and thus contain some small percentage of its energy in flexural wave modes, it will be referred to as "axisymmetric" herein for simplicity. Likewise, flexural wave reflections 23 may contain a large percentage of axisymmetric wave mode energy if they are reflected from generally axisymmetric reflectors such as welds or flanges, or they may only contain a small amount of axisymmetric wave mode energy if reflected from generally non-axisymmetric reflectors such as corrosion, erosion cracks, tees, branches, pipe supports, or other pipe features. These reflections, for simplicity, will be generally referred to as "flexural" herein.

FIG. 3 illustrates a conventional long-range guided wave pipe inspection (LRUT) system. Conventional LRUT technologies utilize a transducer collar 31 that is wrapped around the circumference of pipe 20. Collar 31 is populated with a number of transducer modules 32-1 through 32-32 ("transducers" 32); a larger-diameter pipe requires a pipe collar with more transducers to cover the entire circumference, and a smaller-diameter pipe requires fewer transducers 32. FIG. 3 also illustrates how the plurality of transducers 31 in a conventional LRUT collar are wired together to form transducer segments 33-1 through 33-8 ("segments" 33). Conventional LRUT collars are generally limited to 8 segments, regardless of the diameter of the pipe, thus a larger diameter pipe has more transducers 32 in each segment 33, and a smaller-diameter pipe has fewer. Each segment 33 is wired to an independent pulser/receiver channel, which allows the system to record the circumferential distribution of reflected guided wave energy 23 with limited resolution. The magnetostrictive guided wave pipeline inspection system overcomes this limitation by replacing the segmented transducer collar 31 with an axisymmetric pulser collar and a scanning receiver, as detailed in FIG. 4.

Figure 4:
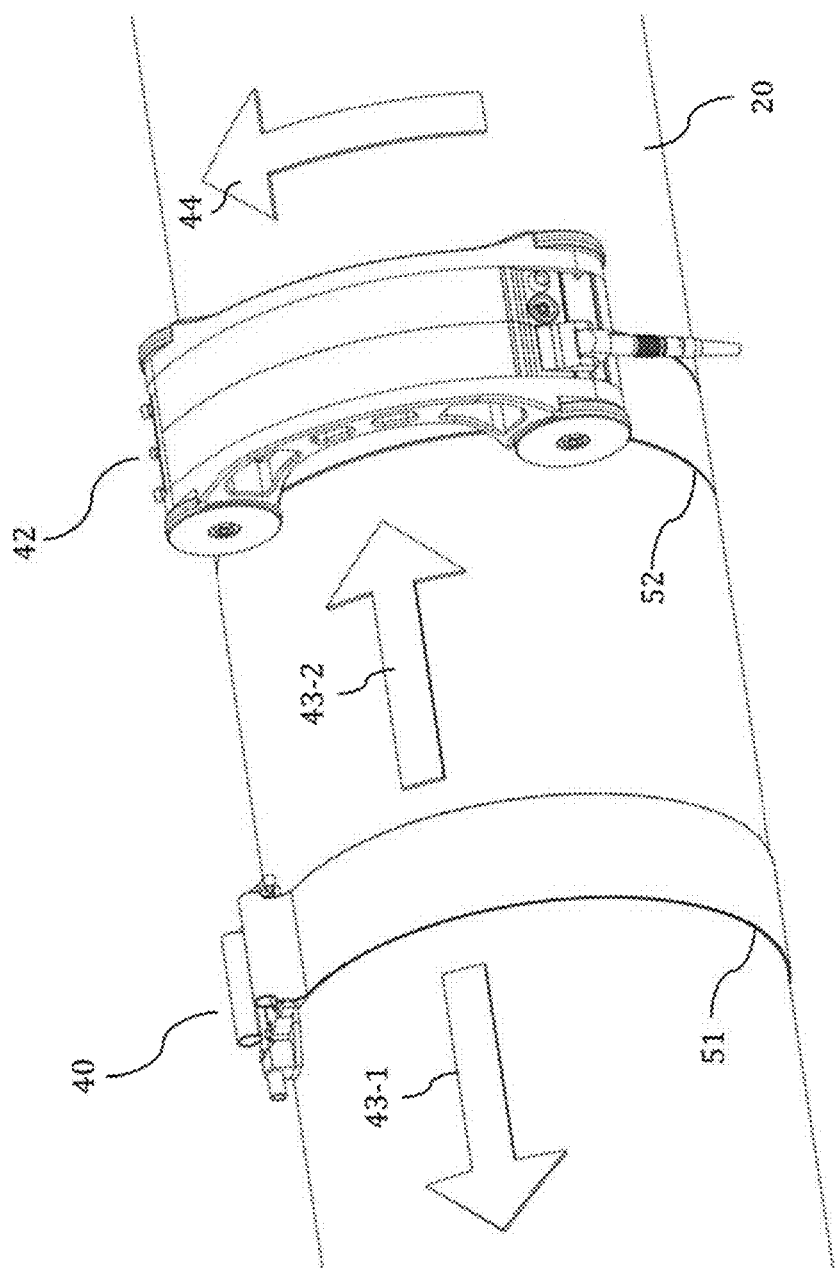
FIG. 4 is a conceptual illustration of the system applied to a pipe.

FIG. 4 illustrates one embodiment of a magnetostrictive guided wave pipeline inspection system, which utilizes an axisymmetric pulser collar 40 to emit axisymmetric guided waves along the axis of pipe 20 in the forward 43-1, and subsequently, reverse 43-2 directions ("axial direction" 43) and a scanner receiver 42, which is moved in direction 44 around the circumference of pipe 20 to characterize the reflected wave field energy 23. Sender collar 40 is placed adjacent to at least one ferromagnetic strip 51, and receiver 42 is placed adjacent to at least one ferromagnetic strip 52.

Figure 5:
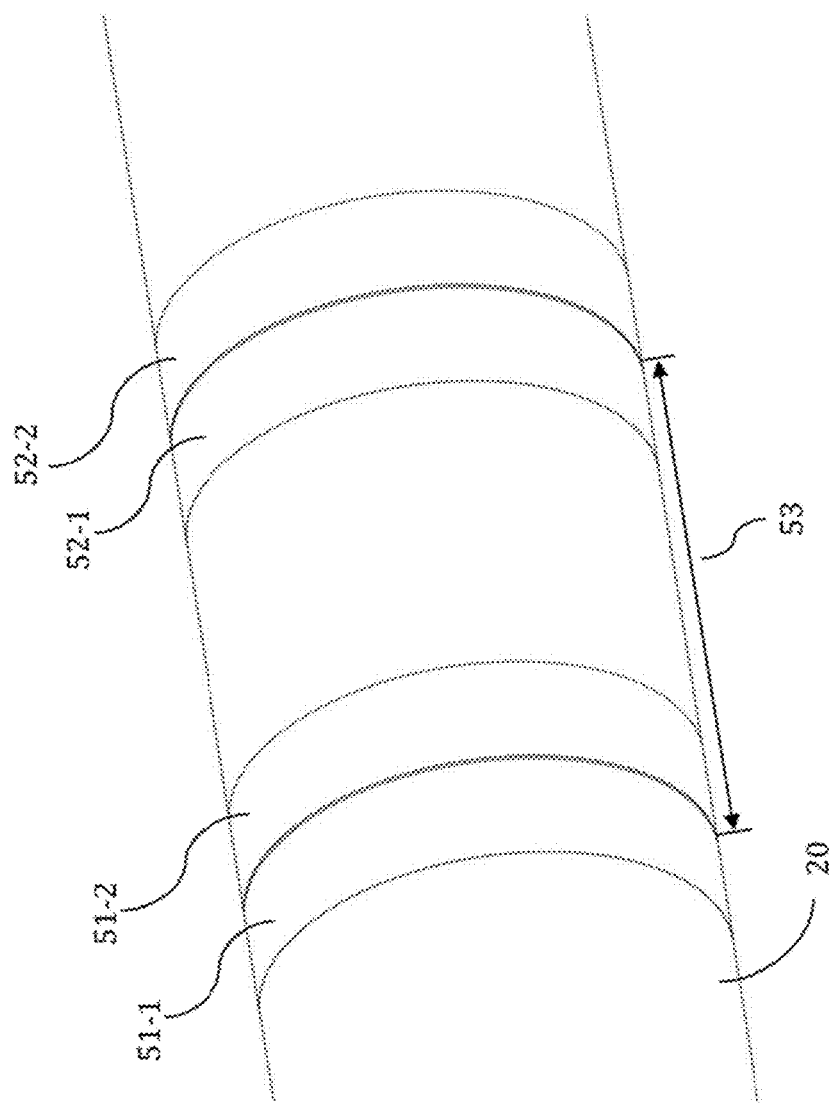
FIG. 5 is an illustration of two sets of ferromagnetic strips coupled to a pipe as components of one embodiment of the system.

FIG. 5 illustrates one embodiment of the ferromagnetic strips 51, 52. In this embodiment, ferromagnetic strips 51-1 and 51-2 ("pulser strips" 51) are coupled to pipe 20 and the axisymmetric pulser collar 40 is placed adjacent to said strips 51. Also in this embodiment, ferromagnetic strips 52-1 and 52-2 ("receiver strips" 52) are coupled to pipe 20 and the scanner receiver 42 is placed adjacent to said strips 52. In general, pulser strips 51 and receiver strips 52 comprise at least one strip. In some embodiments, at least one ferromagnetic strip comprises both the at least one pulser strip 51 and the at least one receiver strip 52, i.e. the pulser and receiver share the same at least one strip. In embodiments in which pulser strips 51 and receiver strips 52 are separate strips, they are separated by some axial distance 53.

In some embodiments where the separation 53 is non-zero, the initial direct axisymmetric wave pulse 22 emitted by pulser coil 40 is detected by scanning receiver 42 as a means of calibrating the system.

Ferromagnetic strips 51 and 52, are ultrasonically shear coupled to pipe 20, i.e. coupled such that shear stresses may be transferred from strip 51 to pipe 20 and from pipe 20 to strip 52, and vice versa. In some embodiments, this coupling is achieved by means of at least one of viscous shear couplant, bonding, adhesive film, and/or mechanical dry coupling via external pressure. The ferromagnetic strips 51, 52 can comprise any suitable material, such as an iron-cobalt alloy in some embodiments.

Figure 6:
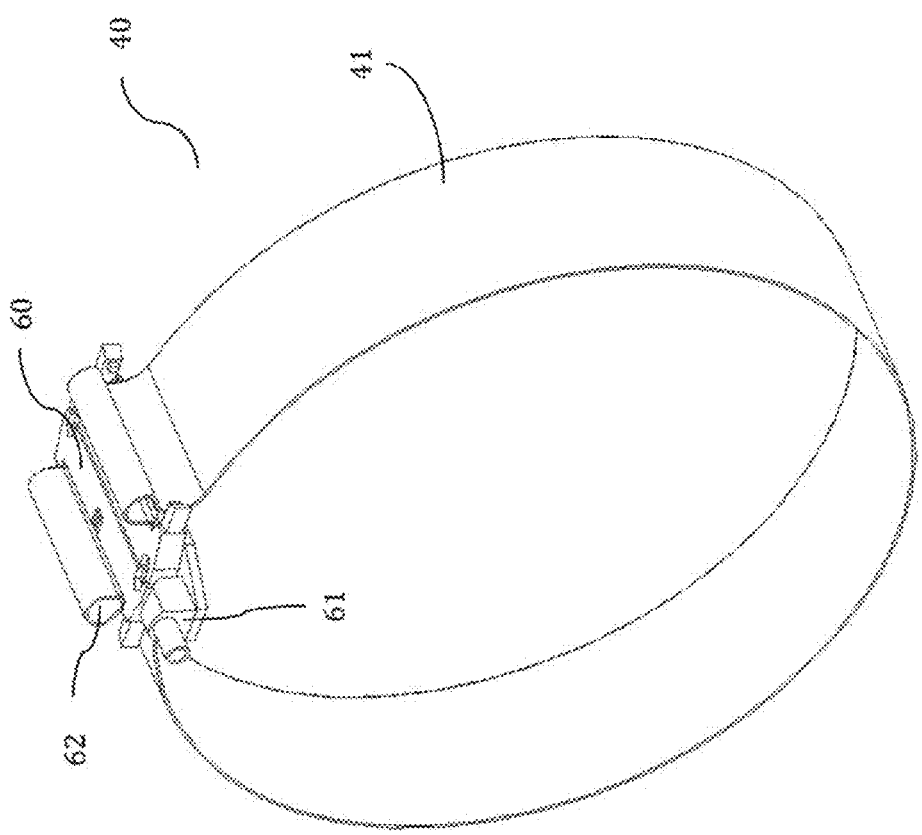
FIG. 6 is an illustration of one embodiment of the axisymmetric pulser collar.

FIG. 6 illustrates one embodiment of the axisymmetric pulser collar 40, which is comprised of at least one coil 41 including a flat, flexible cable (FFC) wrapped around the pipe 20 and placed adjacent to at least one ferromagnetic strip 51. Pulser coil 40 features slack 62 in the FFC to allow said coil 41 to accommodate pipes with a wide range of diameters. Pulser collar 40 generates guided waves in said pipe via the magnetostrictive effect by introducing a time-varying magnetic field in said strips 51 due time-varying currents in said at least one coil 41 in the presence of a biasing magnetic field in said strips 51. Pulser collar 40 is further comprised of a connector board 60 and a connector 61. Connector board 60 is designed such that the parallel traces in the FFC are wired together to form a series of independent coils 41 with predetermined width to control the wavelength of the guided wave modes generated in pipe 20. Connector board 60 is interchangeable to allow the magnetostrictive guided wave pipeline inspection system to generate guided waves across a wide range of frequencies between 10 kHz and 2 MHz. More details on coils 41 are provided in subsequent FIGS. 9a and 9b. Connector 61 is configured to connect pulser coils 41 with the system electronics, which can include a pulser/receiver electronics system, a processor, and/or software to perform data analysis as described in greater detail below. In some embodiments, the FFC axisymmetric pulser collar is replaced with a flexible printed circuit board (FPCB).

FIG. 7a is an illustration of one embodiment of a scanner receiver 42 adjacent to ferromagnetic strip 52 that is coupled to pipe 20 and defines a path along which scanner 42 is moved. Scanner receiver 42 includes a probe body 73 in or on which at least one flexible printed circuit board (FPCB) receiver coil 74, a connector 72, and a position encoder 71 are mounted. In one embodiment, at least one permanent magnet 70 is configured to be stored in said probe body 73. Optical position encoder 71 is mounted on or within probe body 73 and is configured to provide position information to said system electronics by means of a cable between said probe and said electronics. Likewise, connector 72 is configured to provide information on the received guided wave energy to said system electronics.

Figure 7B:
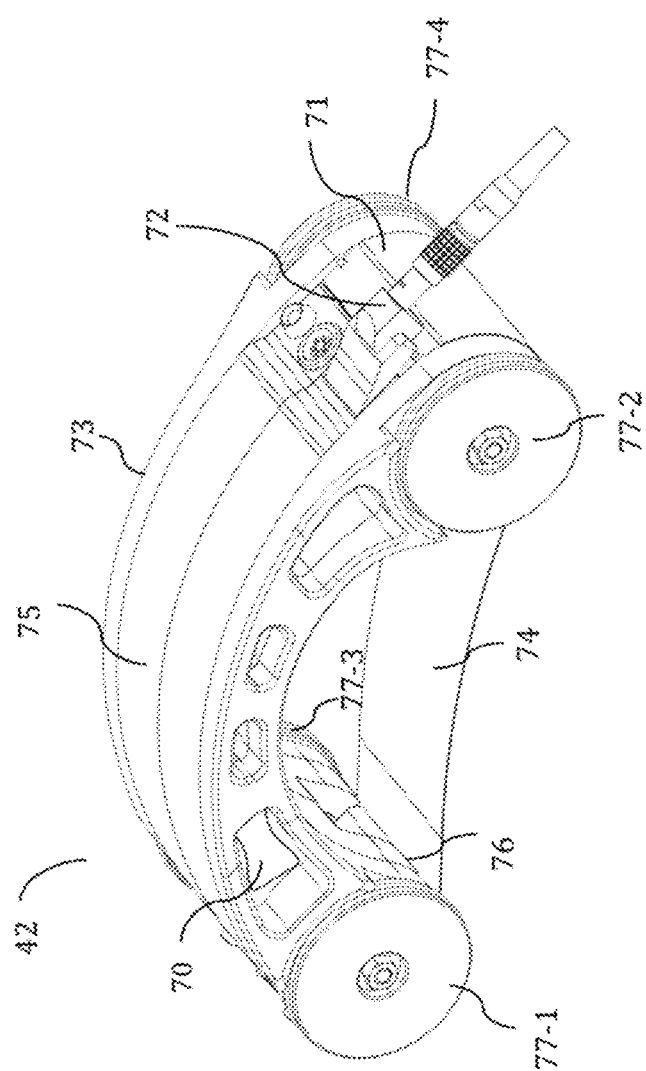
FIG. 7b is an illustration of further details of one embodiment of the scanning receiver.

FIG. 7b illustrates further details of one embodiment of the scanner receiver 42 beyond those described in FIG. 7a, including non-conductive probe core 75, at least one permanent biasing magnet 76, and magnetic front wheels 77-1 and 77-2 as well as magnetic rear wheels 77-3 and 77-4 ("wheels" 77), which provide means for holding scanner 42 in contact with ferromagnetic pipes. The core 75 of probe body 73 that is above the receiver coil 74 is composed of a non-conductive material, including but not limited to acetal, HDPE, and/or ABS plastics, such that it does not interfere with the performance of said magnetostrictive receiver coil 74.

In some embodiments, the permanent magnet 70 that may be stored in the probe body 73 is used as means of inducing biasing magnetization in at least one of pulser strips 51 and receiver strips 52. In some embodiments, at least one electromagnet provides the means for inducing said biasing magnetization in at least one of pulser strips 51 and receiver strips 52. In additional embodiments, the at least one permanent magnet 76 is configured to induce said biasing magnetization in the at least one ferromagnetic receiver strip 52 as scanner receiver 42 is scanned along said strip.

In some embodiments, an impedance matching network, which is generally comprised of at least one of a resistor and/or a capacitor and is connected in series between the ultrasonic pulser/receiver 170 and at least one of pulser coil 41 and receiver coil 74, is utilized in conjunction with at least one of the pulser coil and the receiver coil.

FIG. 8 is an illustration of one embodiment in which pulser collar 41 and scanner receiver 42 are collocated on pipe 20 adjacent to at least one ferromagnetic strip 51. In this embodiment, pulser strips 51 and receiver strips 52 are one in the same.

FIG. 9a provides more details on a general magnetostrictive pulser/receiver coil 90, which is generally representative of the at least one FFC pulser coils 41 and the at least one FPCB receiver coils 74. Coil 90 includes a plurality of straight horizontally extending parallel line segments 92 spaced at periodic interval 91 which is approximately equal to the wavelength of the guided waves that the coil is intended to optimally detect and a plurality of vertically extending line segments 94 connecting line segments 92. Aperture 94 is defined as the width of the parallel horizontally extending coil traces 92. The free ends of the circuit traces are connected to the pulser/receiver 170 (system electronics) described in more detail below with respect to FIGS. 17a and 17b.

FIG. 9b illustrates one embodiment in which receiver coil 74 includes at least two separate coil elements 95-1 and 95-2 ("coils 95") that are aligned parallel to the axial wave propagation direction 43 and separated by some offset 96 that are utilized to calibrate the probe by sending a guided wave between the at least two coil elements 95 while said receiver is moved along strip 52. Offset 96 is defined as the center-to-center separation distance between the at least two coils 95 and may be such that said coils are partially overlapping.

In some embodiments, the at least two separate coil elements 95 include at least one of pulser coil 41 and receiver coil 74 and are independently controlled and utilized to achieve directional wave control by applying at least one of real-time time delays and synthetically-applied post-processing time delay based on the phase velocity and frequency of the guided waves and offset 96 of coils 95 in order to cancel the forward-propagating or reverse-propagating waves, respectively. In the case of torsional guided wave mode pulsing and receiving, at least two independent pulser coils 41 and at least two independent receiver coils 74 are required to achieve directional wave control. In the case of longitudinal guided wave mode excitation and sensing, at least three independent pulser coils 41 and at least three independent receiver coils 74 are required to achieve directional wave control and guided wave mode control.

Figure 10A:
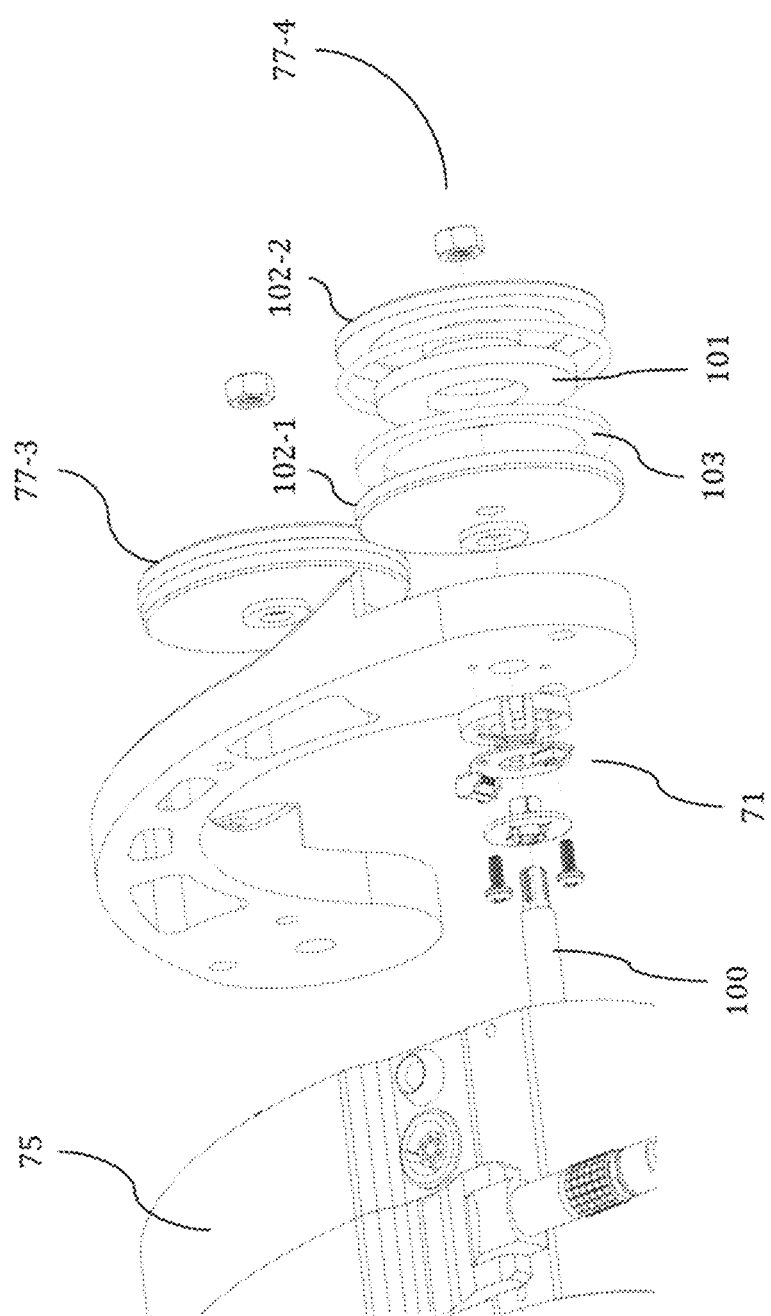
FIG. 10a is an illustration of internal encoder and magnetic wheel components of one embodiment of the scanning receiver.

FIG. 10a illustrates one embodiment of the scanner receiver 42. In some embodiments, the position encoder 71 is located within an internal compartment defined by the probe body 73 and is mounted directly to one of the probe axles 100 such that the position encoder 71 need not be in direct contact with the structure being scanned. In some embodiments, said encoder 71 can be mounted internally or externally to the probe body 73 such that the position encoder 71 is in contact with the pipe 20 being scanned. In some embodiments, the wheels 77 are magnetic to maintain contact with said pipe, while in other embodiments, the wheels are not magnetic. In embodiments for which the wheels 77 are magnetic, said wheels 77 include an inner magnetic core 101, outer wheel plates 102-1 and 102-2 ("wheel plates" 102) composed of a suitable material, such as mildly-magnetic stainless steel, and in contact with core 101, and at least one non-magnetic ring 103 between wheel plates 102.

Figure 10B:
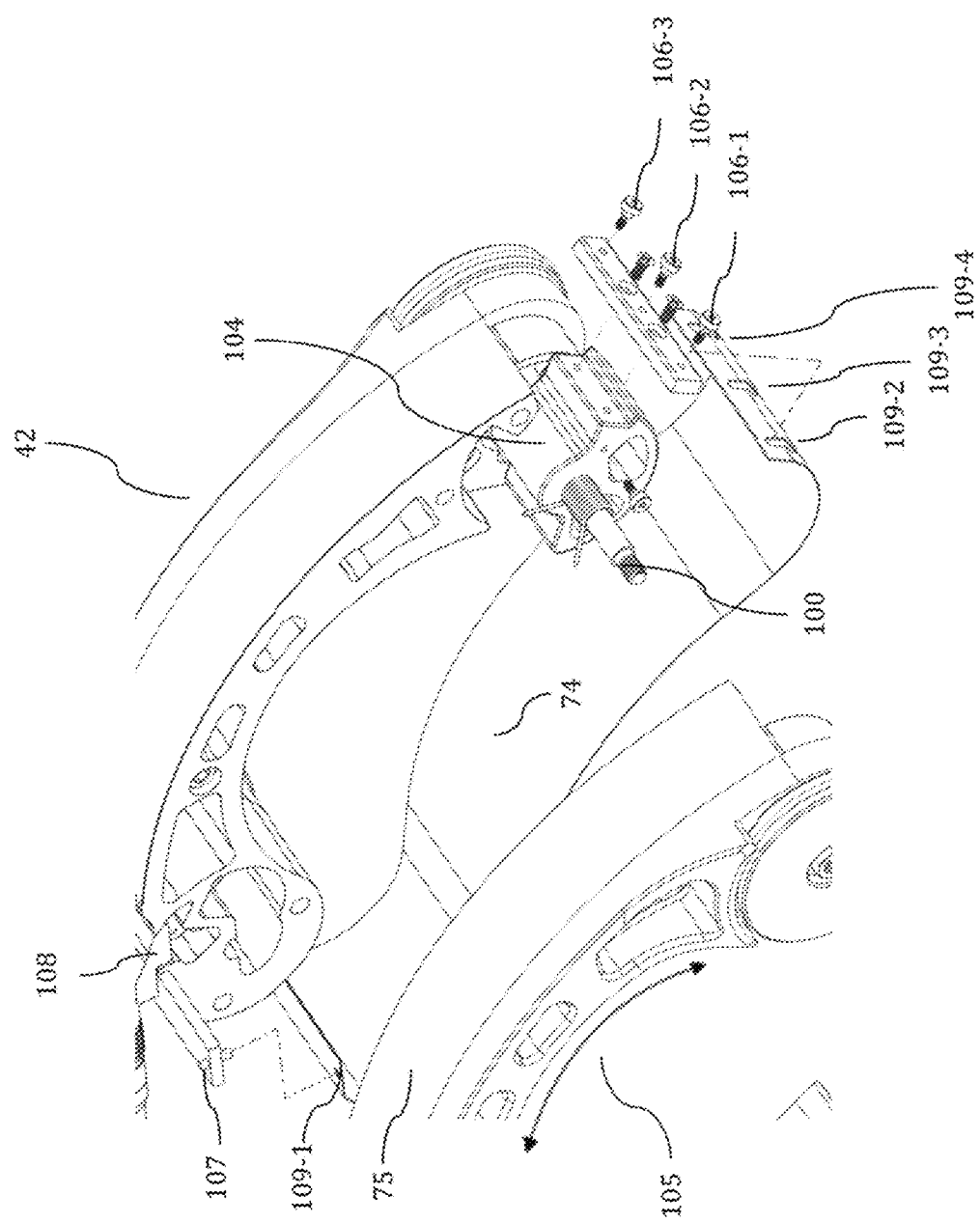
FIG. 10b is an illustration of internal and external coil tensioner and adjustment components of one embodiment of the scanning receiver.

FIG. 10b further illustrates one embodiment of the scanner receiver 42. In some embodiments, receiver coil 74 is interchangeable to easily facilitate replacement or use of a coil with different functional properties, some examples of which have been described in detail elsewhere in this description. For example, and as best seen in FIG. 10b, a set of hooks 106-1, 106-2, and 106-3 ("hooks" 106), a pair of pins 107, corresponding holes 109-1, 109-2, 109-3, and 109-4 ("holes" 109) on said flexible receiver coil 74, and spring-loaded coil capture device 108 facilitate the easy removal and installation of receiver coils without a need for adjusting any fasteners. In some embodiments, the receiver coil 74

Probe body 73 is designed with a curvature 105 that allows it to accommodate pipes 20 with a predefined range of diameters in conjunction with coil tensioner 104. For example, in some embodiments, the probe body 73 is configured to accommodate pipes 20 and/or other structures having a diameter of about 4.5", a diameter of 4.5" or greater, a diameter of 4.5" or smaller, and/or any combination of diameters. Coil tensioner 104 works by placing tension on the flexible receiver coil 74 with a cam and torsion spring coil tensioner 104, which allows the length of said coil 42 in contact with the pipe to change according to the diameter of said pipe while wheels 77 remain in contact with said pipe.

Figure 11B:
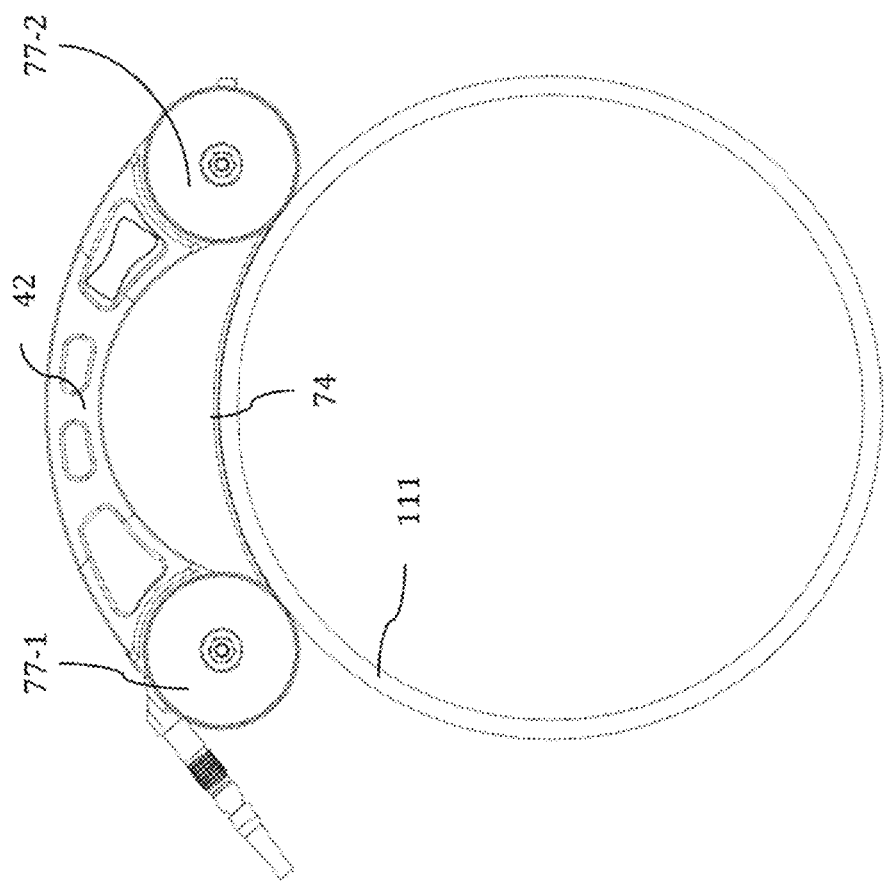
FIG. 11b is an illustration of one embodiment of the scanning receiver applied to an 8" NPS pipe.

FIGS. 11a and 11b further illustrate this concept for a smaller-diameter 4" NPS pipe 110 in FIG. 11a and a larger-diameter 8" NPS pipe 111 in FIG. 11b. In some embodiments, the scanner receiver 42 is designed to accommodate pipe diameters 4" NPS (4.5" outer diameter) and greater, up to and including flat plates (i.e., infinite diameter). In some embodiments, the probe 42 is designed to accommodate pipe diameters ¼" NPS (0.5" outer diameter) and greater, up to and including flat plates (i.e., infinite diameter).

Figure 12A:
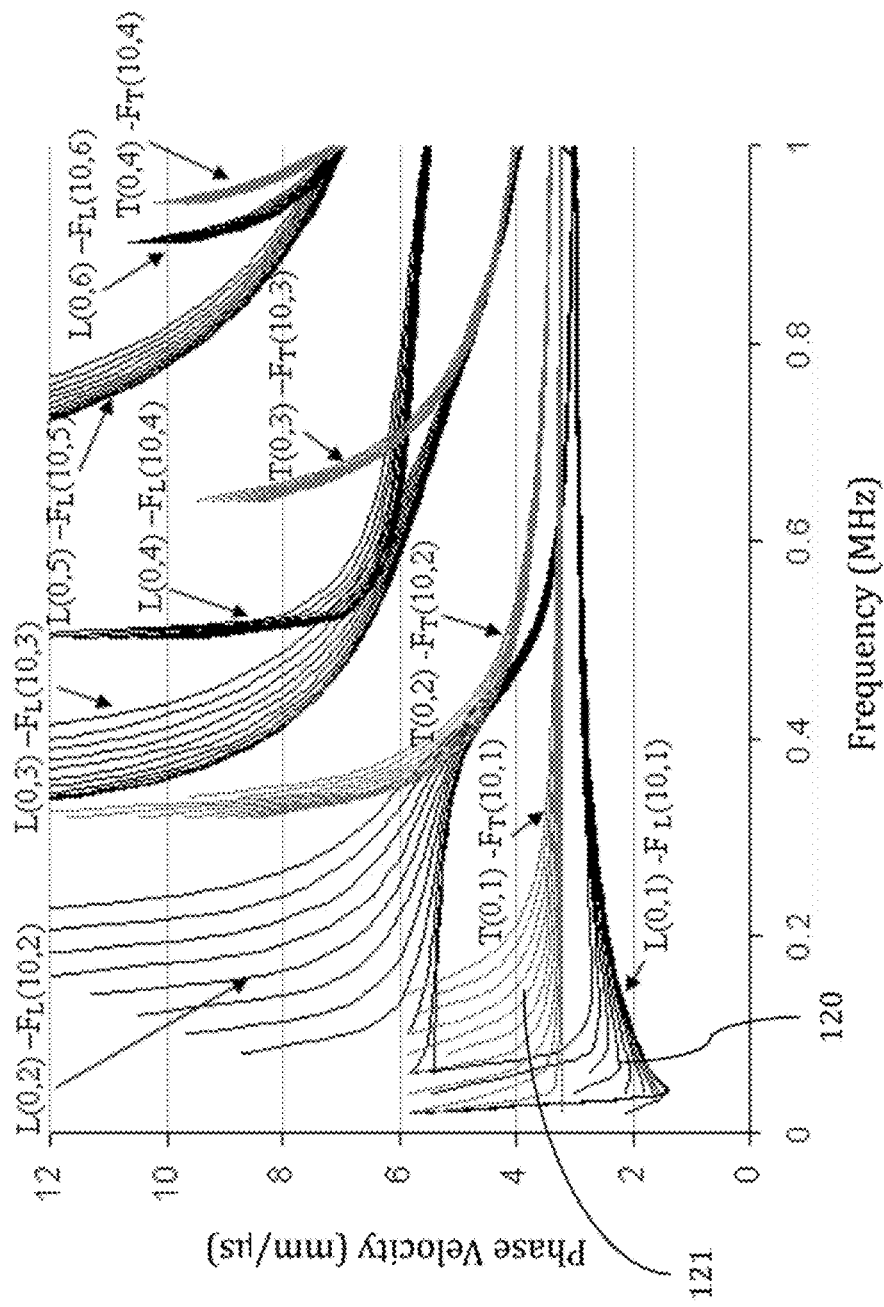
FIG. 12a is an example of pipe dispersion curves showing longitudinal and torsional mode families.

FIG. 12a illustrates dispersion curves 120, 121 of guided wave modes in a pipe. Dispersion curves provide information on the number of guided wave modes that exist in a structure across a range of frequencies and also provide information on the velocity of said modes as a function of frequency. The dispersion curves are developed as a solution to guided wave mechanics equations and are dependent on the material of the waveguide structure and the cross-sectional geometry and dimensions of said structure. In the case of axial guided wave pipe dispersion curves, the wave modes are of one of either the torsional (T) type 121 or the longitudinal (L) type 120. Torsional waves 121 feature predominantly in-plane displacement perpendicular to the axial propagation direction, while longitudinal waves 120 feature predominantly out-of-plane displacement and in-plane displacement parallel to the axial propagation direction. The modes are grouped into mode "families" of modes of either the T or L type that have similar displacement and energy profiles through the thickness of the pipe wall. In some embodiments, the lowest-order $L(n,1)$ longitudinal mode family 120 and the lowest-order $T(n,1)$ torsional mode family 121 are selected. Each mode family is comprised of a fundamental axisymmetric mode $T(0,m)$ or $L(0,m)$, respectively, as well as a set of flexural non-axisymmetric modes $T(n \neq 0,m)$ or $L(n \neq 0,m)$, respectively. In some embodiments, the magnetostrictive guided wave pipeline inspection system generates and detects modes in the $T(n,1)$ family, the $L(n,2)$ family, and/or any other suitable family or combination of families.

Figure 12B:
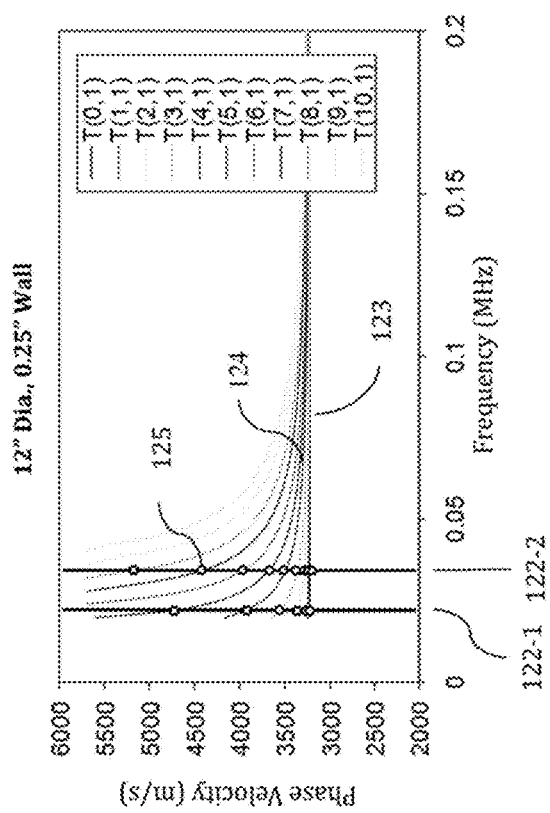
FIG. 12b is a dispersion curve for a 12" NPS×0.25"-thick steel pipe highlighting the T(n,1) mode family at two selected frequencies.
Figure 12C:
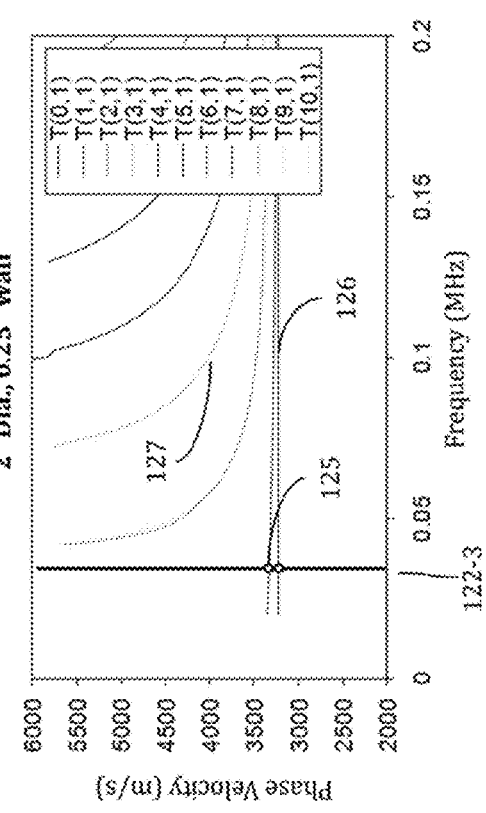
FIG. 12c is a dispersion curve for a 2" NPS×0.25"-thick steel pipe highlighting the T(n,1) mode family at one selected frequency.

FIGS. 12b and 12c provide further details of the $T(n,1)$ family dispersion curves for two different pipe sizes. FIG. 12b illustrates the $T(n,1)$ dispersion curves for a 12"-diameter steel pipe with a 0.25"-thick pipe wall. Vertical lines 122-1 and 122-2 illustrate lines of constant frequency at approximately 25 kHz and 40 kHz, respectively. Points 125 illustrate the intersection of constant-frequency lines 122-1 and 122-2 with the axisymmetric $T(0,1)$ mode dispersion curve line 123 and the flexural $T(n,1)$ mode dispersion curve lines 124. The lower-frequency (25 kHz) line 122-1 intersects six dispersion curve mode lines; while the higher-frequency (50 kHz) line 122-2 intersects nine lines, as more modes exist at high frequencies in a given pipe.

FIG. 12c illustrates the $T(n,1)$ dispersion curves for a 2"-diameter steel pipe with a 0.25"-thick pipe wall. Vertical constant-frequency line 122-3 exists at approximately 40 kHz just like line 122-2 in FIG. 2b. Points 125 illustrate the intersection of constant-frequency line 122-3 with the axisymmetric $T(0,1)$ mode dispersion curve line 126 and the flexural $T(n,1)$ mode dispersion curve lines 127. The line 122-3 only intersects two modes as compared to line 122-2 at the same frequency in FIG. 12c, which intersects nine modes, as fewer modes exist in smaller-diameter pipes than in larger diameter pipes at a given frequency.

In some embodiments, the number of guided wave modes that exist in a pipe of a particular frequency is predetermined to achieve optimum synthetic focusing resolution and inspection speed of the synthetic focusing algorithm as detailed below.

In some embodiments, the two-dimensional synthetic focusing image, i.e. the "unrolled pipe image" or "C-scan image", is generated via a modal decomposition and back-propagation algorithm, such as, for example, the modal decomposition and back-propagation algorithm discussed above. Directly correlating the circumferential location of the receiver that yielded maximum reflection amplitude from a particular feature in the pipe with the true circumferential location and extent of said feature is highly inaccurate because it does not account for the complex wave propagation of the guided wave energy reflected from said feature, as is illustrated by the misalignment of flexural reflection 23 and corrosion defect 21 in FIG. 2. In contrast, the back-propagation algorithm utilized by the magnetostrictive guided wave pipeline inspection system accounts for these complexities and yields highly accurate synthetic focusing results. The ability of the synthetic focusing algorithm to determine the circumferential location and extent of a reflector is limited by the number of partial loading segments with which the guided wave signals were collected. For simplicity, consider a system in which N non-overlapping partial loading segments are used to collect guided wave echoes from one or more features in a pipe. In such a case, the circumferential resolution of the synthetic focusing scheme is limited to the aperture of the individual partial loading segments. For example, in some embodiments, a typical 8-channel segmented pipe inspection collar can only resolve circumferential reflectors to $\frac{1}{8}^{th}$ of the pipe circumference, at best, regardless of the diameter of the pipe. For larger pipe diameters, this is very limiting because it provides poor circumferential resolution, which is critical for data interpretation and characterization and sizing of defects. For example, on a 24" diameter pipe, the lateral resolution of a typical 8-channel segment pipe inspection collar would be limited to 9.4", and on a 48" diameter pipe, the lateral resolution is limited to 18.8". By providing a moveable receiver coil, the number of circumferential receiver locations in the magnetostrictive guided wave pipeline inspection system is less limited. For larger-diameter pipes, more receiving locations can be used to generate more accurate synthetic focusing scans and provide greatly improved circumferential resolution. For example, in the case of an 8" NPS pipe, the resolution can be improved by approximately a factor of 2.5 at 60 kHz. In larger-diameter pipes and at higher frequencies, the improvements in resolution are even greater. For example, in a 24" NPS pipe at 120 kHz, the resolution can be improved by approximately a factor of 13.5 over conventional LRUT. Furthermore, the number of flexural modes $T(m \neq 0, 1)$, which are used in the algorithm to determine the circumferential location and extent of reflectors in the pipe, are limited in all cases. At a particular frequency, larger-diameter pipes will have more flexural modes than equivalent smaller-diameter pipes. The use of N partial loading receiver locations allows the synthetic focusing algorithm to decompose the signals into $N/2+1$ unique guided wave modes including the one axisymmetric mode and $N/2$ flexural modes. If M flexural modes exist in a particular pipe at a particular frequency and N/2<M, aliasing will occur in the wavenumber domain which can yield inaccuracies and less than optimal focusing resolution.

Figure 13A:
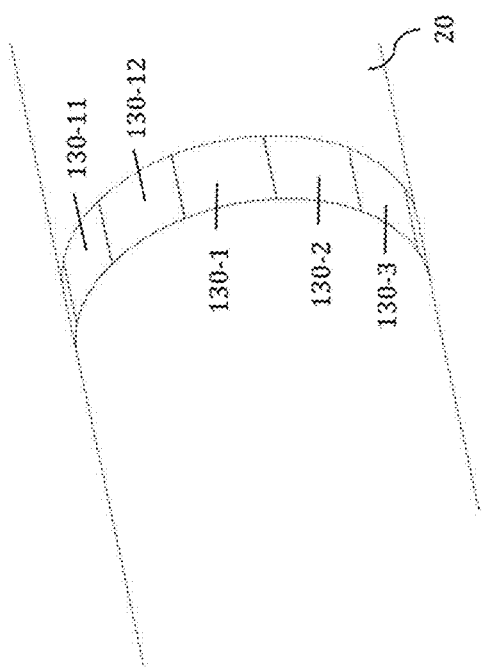
FIG. 13a is an illustration of the minimum receiver segmentation of a 12" NPS×0.25"-thick steel pipe at approximately 25 kHz.
Figure 13B:
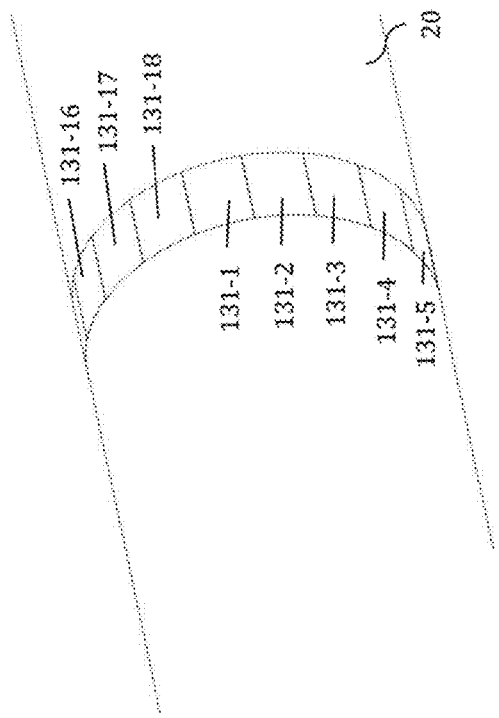
FIG. 13b is an illustration of the minimum receiver segmentation of a 12" NPS×0.25"-thick steel pipe at approximately 40 kHz.

In some embodiments, the magnetostrictive guided wave pipeline inspection system utilizes user-defined pipe information to determine the necessary number of receiver locations to achieve maximum circumferential resolution based on the number of flexural guided wave modes that exist at the frequency at which the inspection is being performed. FIGS. 13a and 13b illustrate receiver scanning segmentation for a 12"-diameter pipe at approximately 25 kHz and 40 kHz, respectively.

Referring to FIG. 13a, a pipe's circumference is evenly divided into N=12 receiver segments 130-1 through 130-12 ("segments" 130), which meets the N/2≥M condition to achieve optimum lateral resolution at a frequency of 25 kHz in said pipe based on the existence of M=6 wave modes T(0,1) through T(5,1) at said frequency in said pipe as illustrated in FIG. 12b.

Referring to FIG. 13b, the pipe's circumference is evenly divided into N=18 receiver segments 131-1 through 131-18 ("segments" 131), which meets the N/2≥M condition to achieve optimum lateral resolution at a frequency of 40 kHz in said pipe based on the existence of M=9 wave modes T(0,1) through T(8,1) at said frequency in said pipe as illustrated in FIG. 12c.

The segments 130 and 131 in FIGS. 13a and 13b represent the location of the receiver coils 74 on the pipe. In some embodiments, the aperture 94 is such that receiver coils 74 extend beyond but are generally centered within an individual segment 130. In some embodiments, said segments 130 partially overlap one another, which can be advantageous for improving signal amplitude.

It should be acknowledged that the axisymmetric wave pulse emitted by the pulser collar is of finite temporal length and is, generally, not purely axisymmetric, and thus neither the emitted energy nor the reflected energy exists purely at a single frequency. Rather, the guided wave energy is distributed within some limited frequency bandwidth. This frequency bandwidth, as well as the dispersion that is associated with it, is accounted for during the back-propagation synthetic focusing algorithm. Hence, to accommodate frequency content that exists above the center-frequency of the emitted axisymmetric wave pulse and the corresponding content that is detected by the scanner receiver, several additional wave modes and thus several more receiver segments may be required than might be otherwise expected based on said center-frequency. This is accounted for by the system algorithms as the approximate frequency bandwidth of the pulse is understood and thus the dispersion curve solutions can be calculated at frequencies within a reasonable bandwidth around the pulsing center frequency to determine the minimum number of scanning segments required to achieve maximum practical resolution.

Figure 14A:
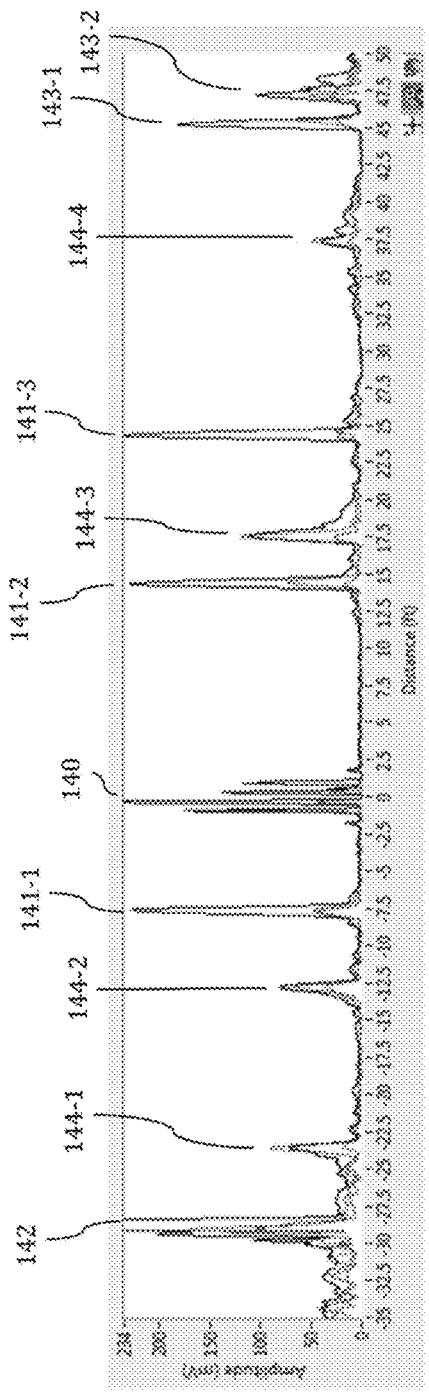
FIG. 14a is an example of a one-dimensional A-scan image of an 80'-long 8" pipe loop generated with the system and method.
Figure 14B:
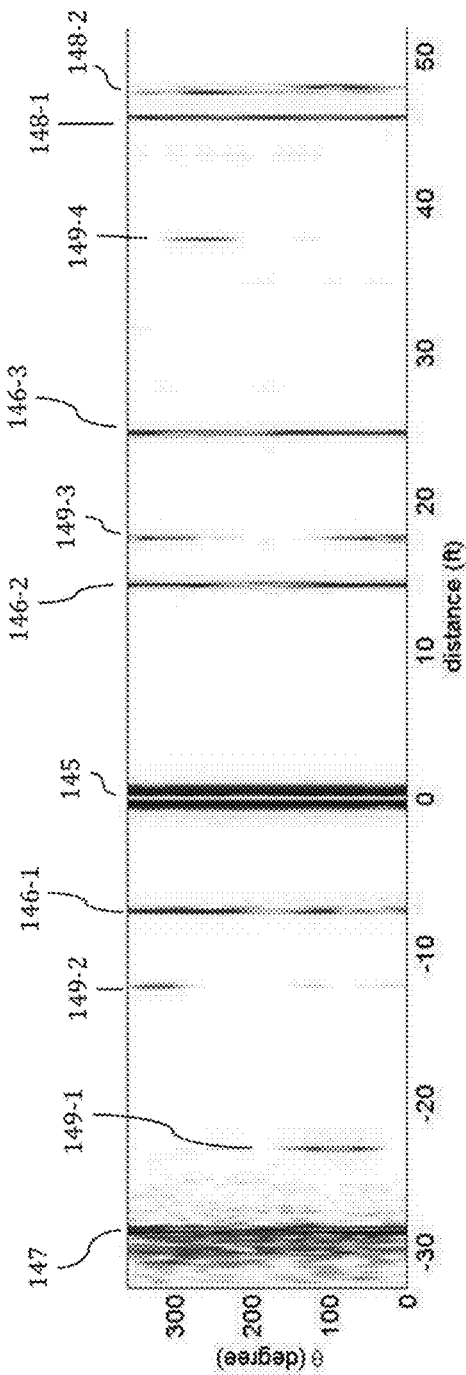
FIG. 14b is an example of a two-dimensional synthetic focusing image of an 80'-long 8" pipe loop generated with the system and method.

FIGS. 14a and 14b are examples of one embodiment of a one-dimensional "A-scan" and a two-dimensional synthetic focusing scan, respectively, which were generated using a magnetostrictive guided wave pipeline inspection system applied to an 80' length of pipe with simulated corrosion defects and a variety of structural features. The 8"-diameter length of pipe features a flange at the left end and a short-radius welded elbow at the right end. The pulser collar 40 and scanner receiver 42 were coupled to the pipe approximately 28' to the right of the flange and 45' left of the elbow. The location of the pulser 40 and receiver 42 is hereafter referred to as "0 feet", and the convention of negative distances to the left and positive distances to the right relative to this 0 position is hereafter adopted when referring to said pipe. Girth welds were present at approximately −7', +14', and +24'. Simulated corrosion defects (drilled spherical pits) were present at approximately −23', −12', +17', and +37'.

FIG. 14a illustrates an A-scan collected on the pipe loop described above at a center frequency of 64 kHz. The horizontal axis in FIG. 14a denotes axial distance along the pipe and the vertical axis denotes reflected wave amplitude. While multiple lines (one black line and two gray lines) are present in this A-scan, only the black line is pertinent for this description. The black line is generated using a method which entails summing the waveforms received by the scanner receiver at all positions, filtering said summed waveform, and enveloping said waveform. The A-scan provides indications of the presence of all anomalies in the pipe. Weld reflections 141-1, 141-2, 141-3, flange reflection 142, elbow weld reflections 143-1,143-2, and defect reflections 144-1, 144-2, 144-3, 144-4. Indication 140 at the 0 location is referred to as the "dead zone" of the inspection and is due to saturation of the receiver electronics due to the emitted axisymmetric wave pulse. However, the limited information in the A-scan of FIG. 14a makes it very challenging to differentiate the non-critical structural features from the critical corrosion defects. Furthermore, it is impossible to determine the lateral extent of said reflectors, which would provide information that is critically important for distinguishing non-critical structural features from critical defects as well as characterizing the dimensions of said defects.

FIG. 14b illustrates a synthetic focusing scan, i.e. "unrolled pipe image" or "C-scan" image, generated from multiple A-scans, such as the one in FIG. 14a. The horizontal axis in FIG. 14a denotes axial distance along the pipe and the vertical axis denotes circumferential position around the pipe and is thus configured such that 0° at the lower extreme of said image and 360° at the upper extreme of said image are equivalent. The intensity (darkness) of the synthetic focusing image is representative of the amplitude of the reflections. As described above, the synthetic focusing image is generated by means of a modal decomposition and back-propagation algorithm. The indications due to the dead zone and any generally axisymmetric reflectors, including welds 146-1, 146-2, 146-3, flange 147, and the first elbow weld 148-1, have generally uniform amplitude vertically, i.e. around the circumference of the pipe. Analogously, the non-axisymmetric reflections, including corrosion indications 149-1, 149-2, 149-3, 149-4 and the second elbow weld 148-2, are representative of non-axisymmetric reflectors. Based on the additional information provided by the focused image, the defects are now clearly distinguishable from the non-critical structural features and the circumferential location and extent of said defects can be characterized.

The second weld reflection 148-2 in FIG. 14b is non-axisymmetric because the waves travel a shorter path along the intradose of said elbow than the waves propagating along the longer extradose of said elbow. The reflections from the second weld at the intradose and extradose are clearly distinguishable in the synthetic focusing image.

FIGS. 15a and 15b provide a comparison between a synthetic focusing scan generated by a conventional 8-segment LRUT system and a synthetic focusing scan generated by the magnetostrictive guided wave pipeline inspection system using a 32-segment receiver scan, respectively. Both scans were collected at a 64-kHz center-frequency from the same location of the pipe loop described in reference to FIGS. 14a and 14b. The synthetic focusing scan has a higher resolution of the corrosion defects 154-1, 154-2, 154-3, 154-4 and the corrosion defects 159-1, 159-2, 159-3, 159-4 than the conventional 8-segment LRUT scan. For example, in the case of an 8" NPS pipe, the resolution can be improved by approximately a factor of 2.5 at 60 kHz. In larger-diameter pipes and at higher frequencies, the improvements in resolution are even greater. For example, in a 24" NPS pipe at 120 kHz, the resolution can be improved by approximately a factor of 13.5 over conventional LRUT. Since the improved scan in FIG. 15b better focuses the defect reflections, the amplitude of those reflections is also subsequently larger relative to the noise floor than in the conventional scan. The improved scan also features better resolution of the second elbow weld 158-2 and a reduction in the spurious indications observed in the vicinity of defect indication 154-4 in the conventional scan.

Figure 16:
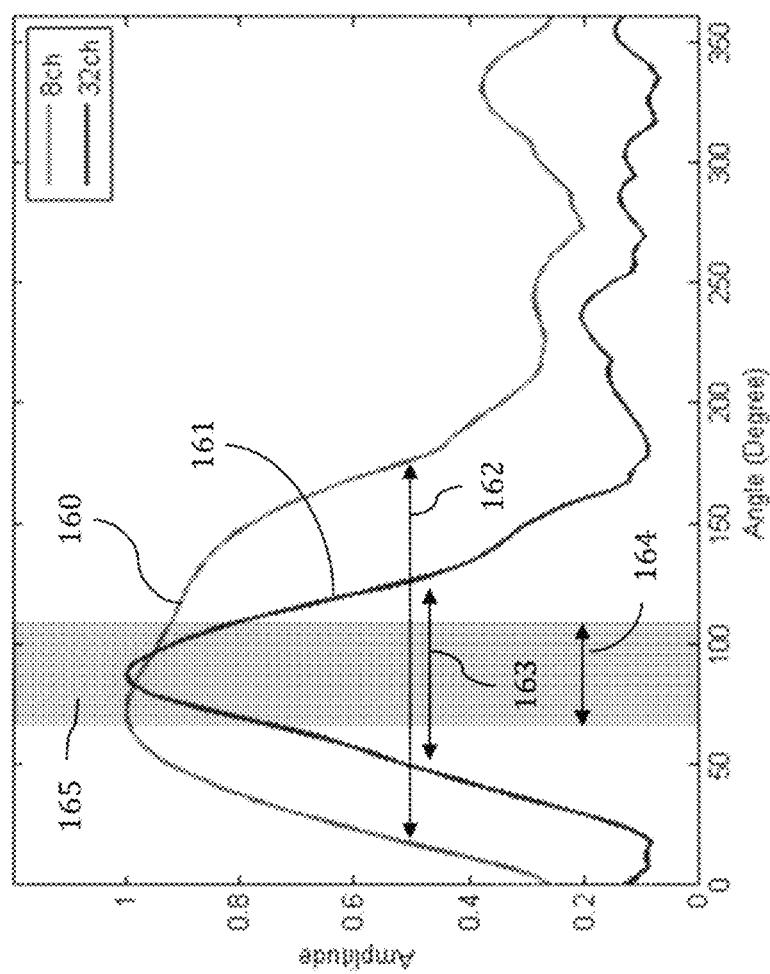
FIG. 16 is a comparison of the cross-section of synthetic focusing images of a simulated corrosion defect generated with a conventional system and method vs. one generated with the disclosed system and method.

FIG. 16 provides a more explicit comparison of one of the synthetic focusing results for the corrosion defect at −23'. Here the horizontal axis denotes circumferential position around the pipe and the vertical axis denotes amplitude of the synthetic focusing image. The gray line denotes the normalized cross-section of the synthetic focusing scan in FIG. 15a at the −23' location, which provides a cross-sectional representation of defect indication 154-1 generated using a conventional LRUT system. Likewise, the black line 161 denotes the normalized cross-section of the synthetic focusing scan in FIG. 15b at the same location, and thus provides a cross-sectional representation of defect indication 159-1 generated using the magnetostrictive guided wave pipeline inspection system. The width 162 of peak 160 is much wider than the width 163 of peak 161; the true lateral extent 164 of said corrosion defect is from approximately 65° to 110°, as illustrated by the gray box 165. The conventional LRUT system greatly overestimates the width of the corrosion defect while the magnetostrictive guided wave pipeline inspection system does so to a much lesser extent. The estimated depth of the corrosion is determined by dividing the amplitude of the reflection by the width of the reflection. Therefore an erroneously wide indication would lead to a reduction in the estimated depth of the corrosion. For example, in the case considered in FIG. 16, the typical 8-channel results predict a defect width of approximately 20°-180° and thus a wall loss of only 18%, while the higher-resolution result from the magnetostrictive guided wave pipeline inspection system described herein predicts a defect width of approximately 50°-130° and thus a wall loss of 37%. The value produced by the guided wave pipeline inspection system is far closer to the true wall loss of 50%. The difference in performance between the typical 8-channel system and the magnetostrictive guided wave pipeline inspection system increases for larger-diameter pipes. A higher-frequency scan with the disclosed magnetostrictive guided wave pipeline inspection system would entail collecting data at more circumferential positions and would continue to increase the lateral resolution of the synthetic focusing, however a higher-frequency scan with a conventional LRUT system would continue to utilize 8 segments and resolution would not improve.

Figure 17A:
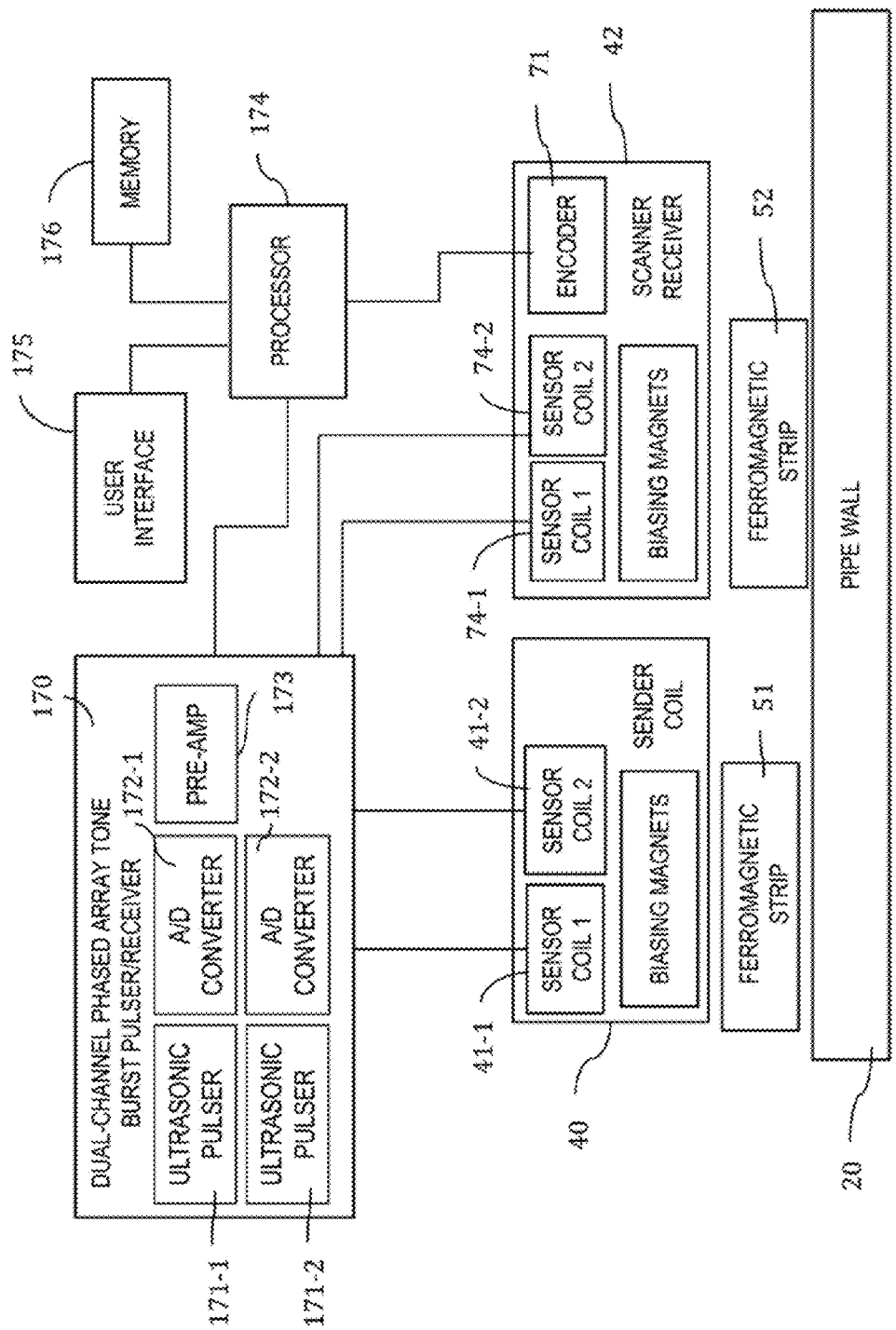
FIG. 17a is a conceptual diagram of a first embodiment of the system electronics.

A schematic illustration of one non-limiting embodiment of the magnetostrictive guided wave pipeline inspection system is provided in FIG. 17a. In this embodiment, the processor 174 and dual-channel phased array pulser/receiver 170 are configured to generate a time-varying current in two pulser coils 41-1 and 41-2 ("pulser coils" 41) as part of pulser collar 40 with a real-time time delay applied between said coils 41 by means of two independent ultrasonic pulser channels 171-1 and 171-2 ("ultrasonic pulsers" 171). Said processor 174 and pulser/receiver 170 are further configured to detect time-varying currents in the two receiver coils 74-1 and 74-2 ("receiver coils" 74) as part of scanner receiver 42. The guided wave signals detected by receiver coils 42 are amplified by at least one pre-amplifier 173 and digitized by means of two independent analog-to-digital converters 172-1 and 172-2 ("A/D converters" 172). The multi-channel ultrasonic pulsers 171 facilitate real-time time delays between a plurality of pulser coils 41 for the purpose of directional wave control and mode control. The multi-channel A/D converters 172 facilitate simultaneous sampling of guided wave signals detected by a plurality of receiver coils 74 for the purpose of directional wave control. Furthermore, the encoder 71 provides position information to the processor to correlate the received guided wave signals with the location of the receiver coil around the circumference of the pipe. The waveform and encoder data are recorded by the machine-readable storage medium 176. User information is provided to the processor and inspection data is provided to the user via the user interface 175.

Figure 17B:
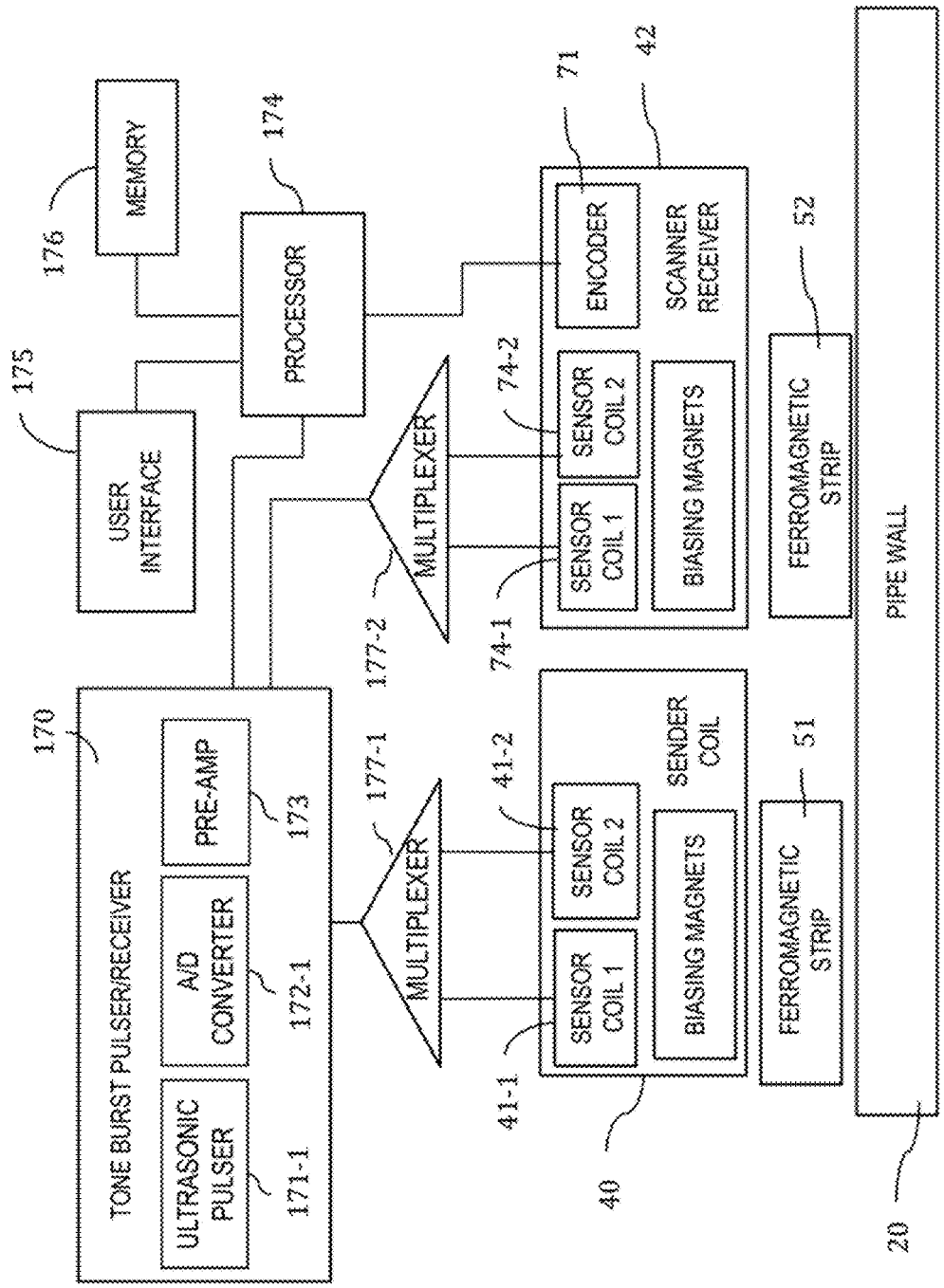

A schematic illustration of another non-limiting embodiment of the magnetostrictive guided wave pipeline inspection system is provided in FIG. 17b. The two independent ultrasonic pulsers 171 are replaced be a single ultrasonic pulser 171-1 and a multiplexer 177-1 and the two independent A/D converters 172 are replaced be a single A/D converter 172-1 and a multiplexer 177-2. In this embodiment, the data acquisition process is repeated on each relevant combination of pulser coils 41 and receiver coils 74, and thereby directional wave control and mode control can be achieved via synthetic time delays applied in post-processing.

Furthermore, additional embodiments of the magnetostrictive guided wave pipeline inspection system may utilize any combination of at least one of multi-channel ultrasonic pulsers 171, a single-channel ultrasonic pulser 171-1 in conjunction with multiplexer 177-1, multi-channel A/D converters 172, and a single-channel A/D converter 172-1 in conjunction with multiplexer 177-2. The implementation of any of said combinations would be apparent to one of ordinary skill in the art and is within the scope of this disclosure.

In some embodiments, system software, by means of a processor, incorporates signal processing techniques to generate and subsequently enhance at least one one-dimensional A-scan image and at least one two-dimensional synthetic focusing image. The signal processing techniques utilized in the software may include, but are not limited to, at least one of averaging, filtering, multi-frequency data acquisition, directional control, reverse wave suppression, modal decomposition, and synthetic focusing, as described herein.

In some embodiments, data is collected at more than one central pulsing frequency to improve defect detection and inspection confidence.

Figure 18:
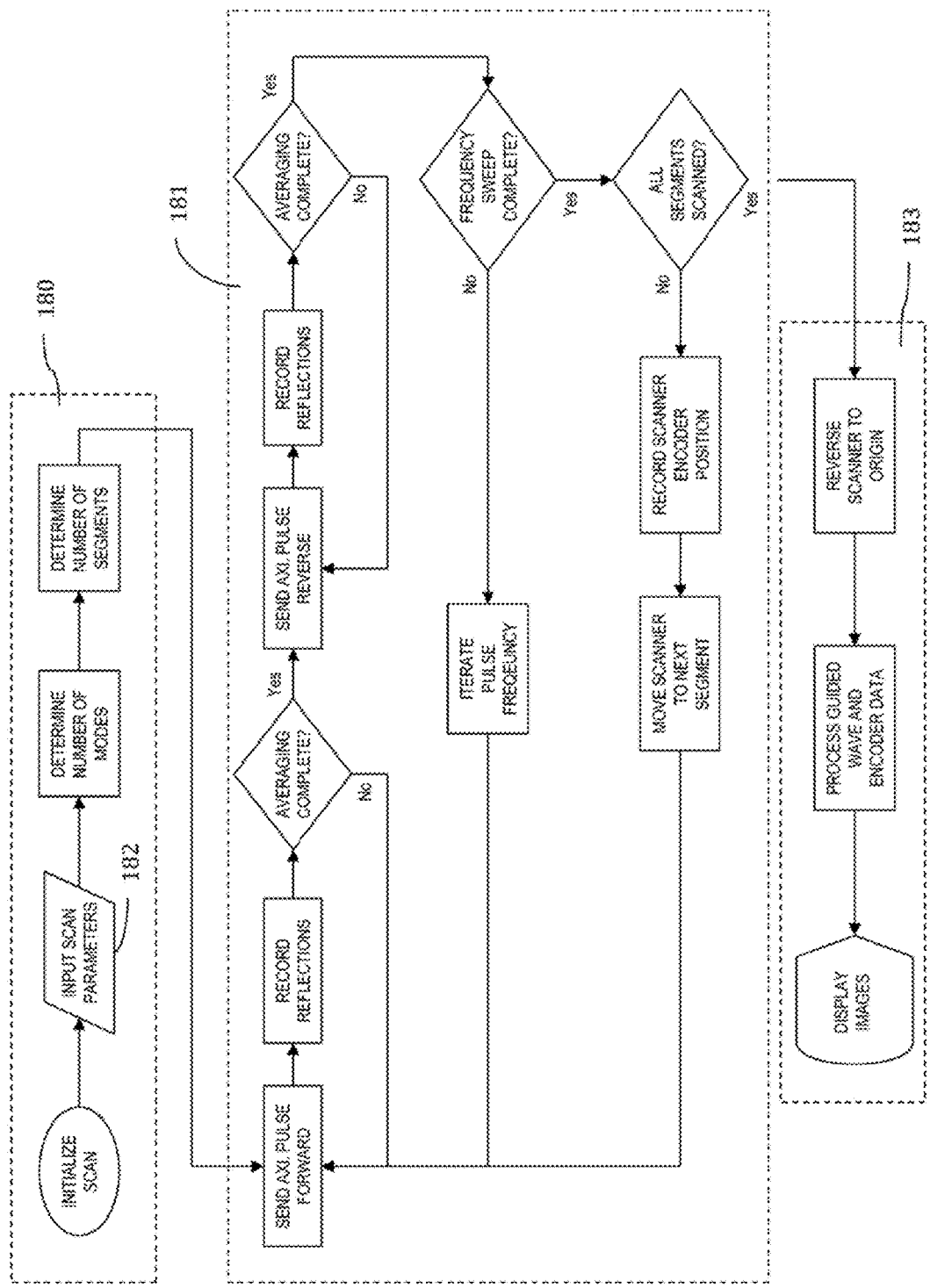
FIG. 18 is a flowchart of one embodiment of the method.

FIG. 18 is a process flow chart providing a high-level illustration of one non-limiting embodiment of the inspection method. In some embodiments, upon initialization of the scan, the scan parameters 182 are provided by the user, including, but not limited to, information relative to the pulser/receiver settings, the geometry and material of the pipe, the guided wave center-frequencies to be utilized, the amount of signal averaging to be utilized, and the length of pipe to be inspected. Based on said scan parameters, the processor determines the number of relevant guided wave modes and the required number of receiver segments around the circumference of the pipe.

Following the initialization process 180, the data collection process 181 is commenced, in which the pulser collar 40 is configured to emit an axisymmetric pulse 22 having a predetermined center-frequency in the "forward" direction 43-1 in conjunction with pulser/receiver 170 and processor 174, and the scanner receiver 42 subsequently detects any guided wave reflections and records said reflections in conjunction with pulser/receiver 170, processor 174, and machine-readable storage medium 176. This pulse-receive process is repeated until all signal averaging has been completed in accordance with the scan parameters 182. Said process is then repeated using a configuration such that the axisymmetric waves having said center-frequency are emitted in the "reverse" direction 43-2.

After recording the requisite forward and reverse data using said process, the process is repeated for any additional center-frequencies in accordance with the scan parameters 182.

After recording the requisite forward and reverse data at all requisite frequencies in accordance with scan parameters 182, the circumferential location of the scanner receiver is recorded by means of position encoder 71, processor 174, and machine-readable storage medium 176. Thereafter, scanner receiver probe 42 is moved to the next receiver segment 130 as defined in initialization process 180, based on the method described above in reference to FIGS. 12*a*, 12*b*, 13*a* and 13*b*, and illustrated in FIG. 13*a*.

After recording the requisite forward and reverse data at all requisite frequencies within all requisite segments in accordance with scan parameters 182, the data collection process 181 is complete, and the data processing process 183 commences. As part of the data processing process 183, the at least one A-scan image and the at least one synthetic focusing image are generated by means of processor 174, machine-readable storage medium 176, and the processes described in detail above.

In some embodiments, said images are displayed for the user by means of user interface 175. In some embodiments, at least some portion of data processing process 183 is conducted in parallel to data collection process 181 for the purpose of improving efficiency. In some embodiments, the frequency iteration process loop and segment iteration process loop may be interchanged.

Figure 19:
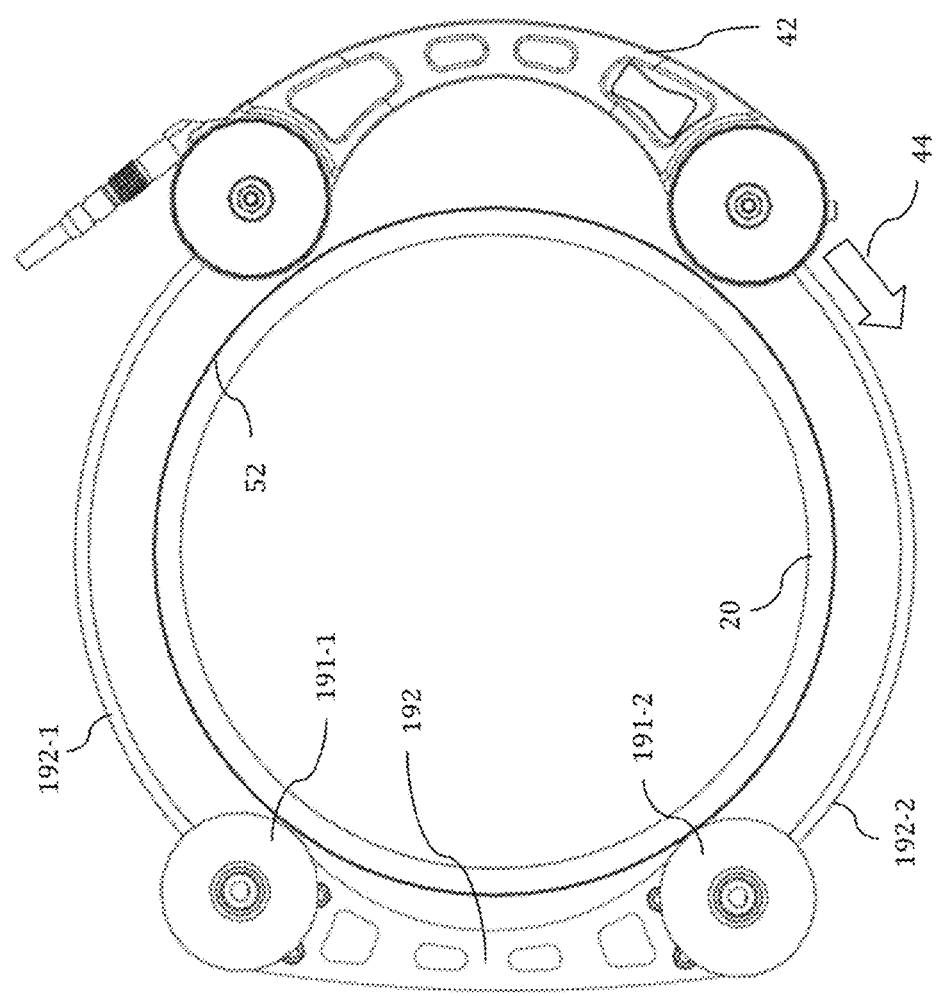
FIG. 19 is an illustration of one automated means of moving the scanning receiver around the circumference of a pipe in accordance with the method.

The movement of scanner receiver 42 is achieved by one of manual or automated means. The automated means of carrying out the scanning action may include, but are not limited to, at least one motorized wheel attached to said scanner receiver 42, a tractor and cable system as illustrated in FIG. 19, and any similar system utilizing actuators or stepper/servo motors. Additional means of moving scanner receiver 42 around the pipe will be obvious to those of ordinary skill in the art.

FIG. 19 illustrates one embodiment in which the means of moving scanner receiver 42 is a tractor and cable system. In this embodiment, a motorized tractor unit 192 is connected to scanner receiver 42 by at least one tensioned cable 192-1 and 192-2 ("cables" 192). Tractor unit 192 features wheels 191-1 through 191-4, which are magnetic wheels similar in design to wheels 77 in some embodiments. Cables 192 assist in maintaining wheel contact with pipe 20 and facilitate motion in direction 44 or in the opposite direction. Tractor unit 192 is in communication with processor 174. The tractor and cable design allows scanner receiver 42 and tractor unit 192 to be compatible with a wide range of pipe diameters and also allows scanner receiver 42 to be disconnected from said tractor and said cables to facilitate manual scanning. In some embodiments, tractor unit 192 is weighted to have similar mass to scanner receiver 42 such that it acts as a counter balance to said receiver and the system always experiences a net rotational moment of zero, which prevents unwanted rotation of the system during scanning.

What is claimed is:

1. A system, comprising:
   at least one axisymmetric magnetostrictive pulser coil;
   at least one ferromagnetic strip configured to be coupled to a structure, wherein said at least one ferromagnetic strip is configured to be located adjacent to said at least one axisymmetric magnetostrictive pulser coil;
   a scanner receiver probe comprising a probe body, a position encoder, and at least one magnetostrictive partial loading receiver coil, wherein the scanner receiver probe is configured to be located adjacent to at least one ferromagnetic strip;
   at least one magnet for applying a biasing magnetic field to said at least one ferromagnetic strip;
   an electronic pulser system configured to generate a time-varying current in said at least one axisymmetric magnetostrictive pulser coil to induce a time-varying magnetization in said at least one ferromagnetic strip in the presence of the biasing magnetic field to generate guided wave energy in said structure, wherein said at least one axisymmetric magnetostrictive pulser coil or said at least one magnetostrictive partial loading receiver coil comprises at least two independent coils, wherein the at least two independent coils are configured to apply a predetermined time delay;
   at least one wheel configured to move said partial loading receiver probe around the circumference of said structure along said ferromagnetic strip, wherein said scanner receiver probe is configured to detect reflected guided wave energy as said scanner receiver probe is moved around the circumference of said structure; and
   a processor configured to
     control said electronic pulser system;
     record guided wave reflections detected by said scanner receiver probe; and
     process said guided wave reflections and said scanner receiver probe position data to generate a two-dimensional image of anomalies in said structure using a synthetic focusing algorithm.

2. The system of claim 1, wherein said guided wave energy are torsional mode families T(m, n), longitudinal mode families L(m, n), or a combination thereof.

3. The system of claim 1, wherein at least one of said at least one axisymmetric magnetostrictive pulser coil or at least one magnetostrictive partial loading receiver coil comprises one of a flat-flexible cable, a flexible printed circuit board, or a combination thereof.

4. The system of claim 1, wherein said at least one axisymmetric magnetostrictive pulser coil and at least one magnetostrictive partial loading receiver coil are collocated adjacent to at least one ferromagnetic strip.

5. The system of claim 1, wherein said at least one axisymmetric magnetostrictive pulser coil and at least one magnetostrictive partial loading receiver coil utilize separate circumferentially-wrapped ferromagnetic strips separated by some axial distance.

6. The system of claim 1, wherein said predetermined time delays are at least one of a real-time time delay applied by means of phased array electronics, a synthetic time delay applied by means of post-processing, or a combination thereof.

7. The system in claim 1, wherein said at least one axisymmetric magnetostrictive pulser coil and at least one magnetostrictive partial loading receiver coil are interchangeable to accommodate one or more coil designs that operate in a range of frequencies from 10 kHz to 2 MHz and with a range of apertures between 10 mm and 200 mm.

8. The system of claim 7, wherein the aperture of said at least one magnetostrictive partial loading receiver coil is determined based on a diameter, a schedule, and a material of the structure and a number of flexural guided wave modes that exist in the structure in the range of frequencies.

9. The system of claim 1, wherein the at least one magnet is one of a permanent magnet, an electromagnet, or a combination thereof.

10. The system of claim 1, wherein the electronic pulser system is one of an electronic tone-burst or square wave pulser system having at least one pulser channel and at least one of multiplexing and phased array capabilities.

11. The system of claim 1, said scanner receiver probe comprises an analog-to-digital converter system having at least one receiver channel and at least one of multiplexing and phased array capabilities configured to detect said reflected wave energy.

12. A method, comprising:
applying, using a magnet, a biasing magnetic field to at least one ferromagnetic strip coupled to a structure;
controlling, using a processor, an electronic pulser system to generate a time-varying current in at least one axisymmetric pulser coil to induce a time-varying magnetization in said at least one ferromagnetic strip in the presence of the biasing magnetic field to generate guided wave energy in said structure, wherein said pulser coil is located adjacent to said at least one ferromagnetic strip;
using a wheel to move a scanner receiver probe, including a probe body, a position encoder, and at least one magnetostrictive partial loading receiver coil, around a circumference of said structure;
detecting reflected guided wave energy using the said at least one magnetostrictive partial loading receiver coil as the scanner receiver probe is moved around the circumference of said structure; and
processing, using the processor, the said reflected guided wave energy and position data of said partial loading receiver scanner using a synthetic focusing algorithm to generate a two-dimensional image of anomalies in said structure,
wherein said at least one axisymmetric magnetostrictive pulser coil or said at least one magnetostrictive partial loading receiver coil comprises at least two independent coils,
and wherein controlling the electronic pulser system to generate a time-varying current includes applying a predetermined time delay to the at least two independent coils.

13. The method of claim 12, wherein the magnet is at least one of a permanent magnet, an electromagnet, or a combination thereof.

14. The method of claim 12, wherein the magnet includes at least one permanent magnet embedded in the scanner receiver probe.

15. The method of claim 12, wherein the scanner receiver probe is moved relative to said structure along said ferromagnetic strip by one of a manual movement of the scanner receiver probe, an automated scanning system, or a combination thereof.

16. The method of claim 12, wherein a number of locations around said circumference of said structure at which said reflected guided wave energy is detected is determined by a diameter, a schedule, and a material of said structure and a number of flexural guided wave modes that exist in said structure in a selected frequency.

17. A system for non-destructive inspection of a structure, comprising:
at least one axisymmetric magnetostrictive pulser coil;
at least one ferromagnetic strip configured to be coupled to said structure, wherein said at least one ferromagnetic strip is configured to be located adjacent to said at least one axisymmetric magnetostrictive pulser coil;
a scanner receiver probe comprising a probe body, a position encoder, and at least one magnetostrictive partial loading receiver coil, wherein the scanner receiver probe is configured to be located adjacent to at least one ferromagnetic strip;
at least one magnet for applying a biasing magnetic field to said at least one ferromagnetic strip;
an electronic pulser system configured to generate a time-varying current in said at least one axisymmetric magnetostrictive pulser coil to induce a time-varying magnetization in said at least one axisymmetric ferromagnetic strip in the presence of the biasing magnetic field to generate guided wave energy in said structure, wherein said at least one axisymmetric magnetostrictive pulser coil and at least one magnetostrictive partial loading receiver coil are interchangeable to accommodate one or more coil designs that operate in a range of frequencies from 10 kHz to 2 MHz and with a range of apertures between 10 mm and 200 mm;
at least one wheel configured to move said partial loading receiver probe around the circumference of said structure along said at least one ferromagnetic strip, wherein said scanner receiver probe is configured to detect reflected guided wave energy as said scanner receiver probe is moved around the circumference of said structure; and
a processor configured to
control said electronic pulser system;
record guided wave reflections detected by said scanner receiver probe; and
process said guided wave reflections and said scanner receiver probe position data to generate a two-dimensional image of anomalies in said structure using a synthetic focusing algorithm.

18. The system of claim 17, wherein the aperture of said at least one magnetostrictive partial loading receiver coil is determined based on a diameter, a schedule, and a material of the structure and a number of flexural guided wave modes that exist in the structure in the range of frequencies.

19. The system of claim 17, wherein the at least one magnet is one of a permanent magnet, an electromagnet, or a combination thereof.

* * * * *